United States Patent
Huber et al.

(10) Patent No.: US 9,638,638 B2
(45) Date of Patent: May 2, 2017

(54) SYSTEM AND METHOD FOR STIMULATED RAMAN SPECTROSCOPY

(71) Applicant: Ludwig-Maximilians-Universität München, München (DE)

(72) Inventors: Robert Alexander Huber, Schnaitsee (DE); Thomas Klein, Munich (DE); Wolfgang Wieser, Munich (DE); Sebastian Karpf, Munich (DE); Matthias Eibl, Witzmannsberg (DE)

(73) Assignee: Ludwig-Maximilians-Universität München, München (DE)

( * ) Notice: Subject to any disclaimer, the term of this patent is extended or adjusted under 35 U.S.C. 154(b) by 0 days.

(21) Appl. No.: 14/890,109

(22) PCT Filed: May 9, 2014

(86) PCT No.: PCT/EP2014/059566
§ 371 (c)(1),
(2) Date: Nov. 9, 2015

(87) PCT Pub. No.: WO2014/180986
PCT Pub. Date: Nov. 13, 2014

(65) Prior Publication Data
US 2016/0091429 A1 Mar. 31, 2016

(30) Foreign Application Priority Data
May 10, 2013 (EP) .................................... 13167325

(51) Int. Cl.
*G01J 3/44* (2006.01)
*G01N 21/65* (2006.01)
(Continued)

(52) U.S. Cl.
CPC ................. *G01N 21/65* (2013.01); *G01J 3/44* (2013.01); *G01J 3/4412* (2013.01);
(Continued)

(58) Field of Classification Search
CPC ........... G01N 21/65; G01N 2201/0697; G01N 2201/06113; G01N 2201/0683; G01J 3/44; G01J 3/4412
(Continued)

(56) References Cited

U.S. PATENT DOCUMENTS 6,560,478 B1 *  5/2003  Alfano ................. A61B 5/0075
                                                       600/473
2010/0046039 A1    2/2010  Xie et al.
(Continued)

FOREIGN PATENT DOCUMENTS

EP            2211219 A2      7/2010

OTHER PUBLICATIONS

Min, "Label-free optical imaging of nonfluorescent molecules by stimulated radiation," Current Opinion in Chemical Biology 15:831-837 (2011).
(Continued)

*Primary Examiner* — Abdullahi Nur
(74) *Attorney, Agent, or Firm* — Marshall, Gerstein & Borun LLP

(57) ABSTRACT

Disclosed herein is a system (10) for measuring light induced transmission or reflection changes, in particular due to stimulated Raman emission. The system comprises a first light source (12) for generating a first light signal having a first wavelength, a second light source (14) for generating a second light signal having a second wavelength, an optical assembly (16) for superposing said first and second light signals at a sample location (18), and a detection means (24) for detecting a transmitted or reflected light signal, in particular a stimulated Raman signal caused by a Raman-active medium when located at said sample location. Here in at least one of the first and second light sources (12, 14) is one or both of actively controllable to emit a time controlled (Continued)

light pattern or operated substantially in CW mode and provided with an extra cavity modulation means (64) for generating a time controlled light pattern. The detection means (24) is capable of recording said transmitted or reflected light signal, in particular stimulated Raman signal, as a function of time.

20 Claims, 13 Drawing Sheets

(51) Int. Cl.

| | | |
|---|---|---|
| *H01S 3/067* | (2006.01) | |
| *H01S 3/10* | (2006.01) | |
| *H01S 3/23* | (2006.01) | |
| *H01S 3/30* | (2006.01) | |
| H01S 3/0941 | (2006.01) | |
| H01S 3/16 | (2006.01) | |
| H01S 3/00 | (2006.01) | |
| H01S 3/094 | (2006.01) | |

(52) U.S. Cl.
CPC ...... *H01S 3/06758* (2013.01); *H01S 3/10015* (2013.01); *H01S 3/2391* (2013.01); *H01S 3/302* (2013.01); *G01N 2021/655* (2013.01); *G01N 2201/0683* (2013.01); *G01N 2201/0697* (2013.01); *G01N 2201/06113* (2013.01); *H01S 3/0064* (2013.01); *H01S 3/0078* (2013.01); *H01S 3/09415* (2013.01); *H01S 3/094069* (2013.01); *H01S 3/1618* (2013.01)

(58) Field of Classification Search
USPC .............................................. 356/301, 72–73
See application file for complete search history.

(56) References Cited

U.S. PATENT DOCUMENTS

2010/0134793 A1    6/2010  Krishnamachari et al.
2014/0218726 A1*   8/2014  Cheng .................. G01N 21/65
                                                356/301

OTHER PUBLICATIONS

Rowen, et al. "A combined Yb-Roman fiber amplifier for generating narrow linewidth, high-power pulses in the 1100-1200 nm wavelength range and efficient nonlinear conversion into Yellow," Proc. of SPIE 8601:86011J-1 to 86011-J-8 (2013).
International Search Report and Written Opinion from PCT/EP2014/059566 dated Jul. 31, 2014.
Zumbusch, et al. "Three-dimensional vibrational imaging by coherent anti-Stokes Raman scattering," Physical Review Letters 82:4142-4145 (1999).
Evans, et al. "Chemical imaging of tissue in vivo with video-rate coherent anti-Stokes Raman scattering microscopy," Proc Nat Acad Sci 102:16807-16812 (2005).
Albrecht, et al. "Anomalously Intense Raman-Spectra of Pyridine at a Silver Electrode," Journal of the American Chemical Society 99:5215-5217 (1977).
Huber, et al. "Fourier Domain Mode Locking (FDML): A new laser operating regime and applications for optical coherence tomography," Optics Express 14(8):3225-3237 (2006).
Owyoung, "CW Stimulated Raman-Spectroscopy," Abstracts of Papers of the American Chemical Society 175:124-124 (1978).
Owyoung, "Sensitivity Limitations for CW Stimulated Raman Spectroscopy," Optics Communications, 22(3):323-328 (1977).
Owyoung et al. "Stimulated Raman spectroscopy using low-power cw lasers," Optics Letters 1(5):152-154 (1977).

* cited by examiner

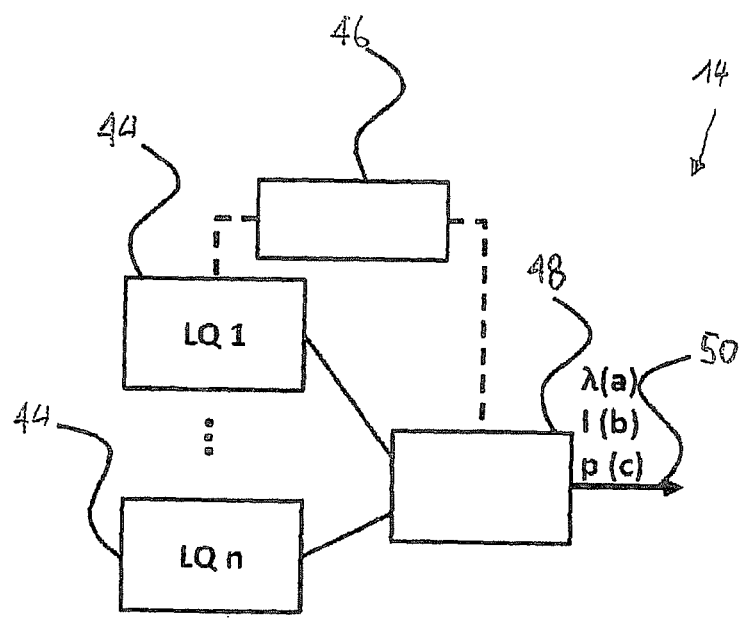
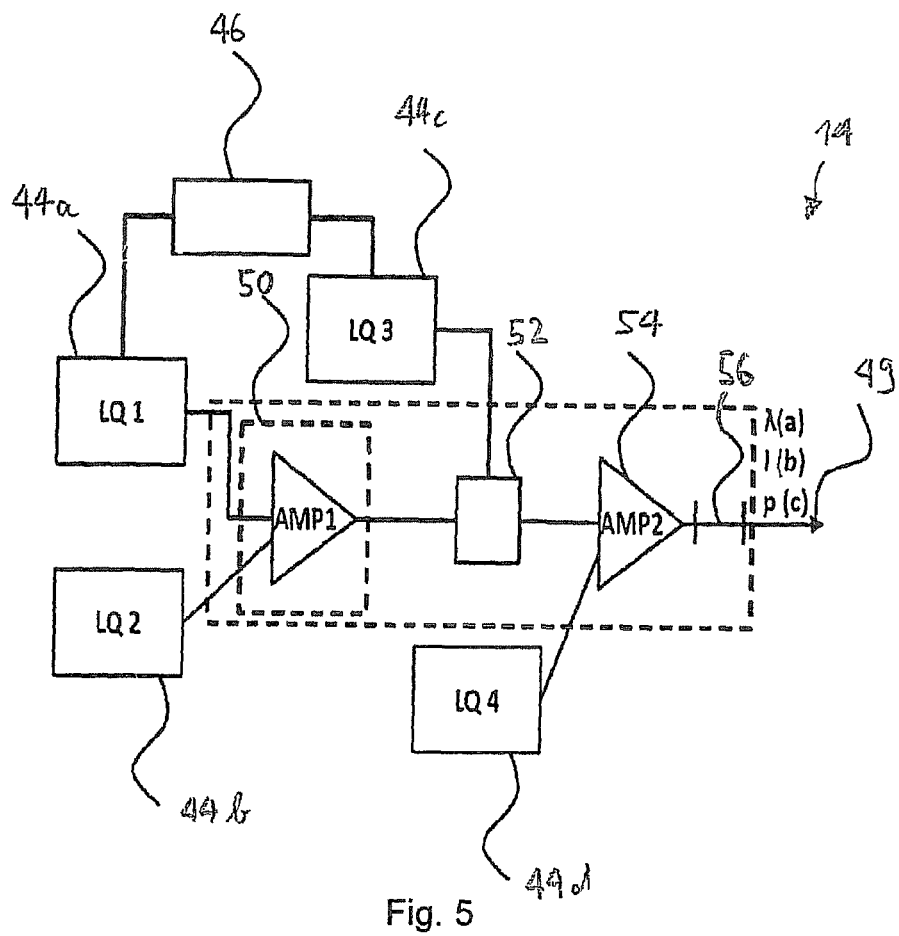
Fig. 4
Fig. 5

SYSTEM AND METHOD FOR STIMULATED RAMAN SPECTROSCOPY

CROSS-REFERENCE TO RELATED APPLICATIONS

This is the U.S. national phase of PCT/EP2014/059566, filed May 9, 2014, which claims the benefit of European Patent Application No. 13167325.3, filed May 10, 2013.

FIELD OF THE INVENTION

The present invention is in the field of optical spectroscopy. In particular, the invention relates to a system and method for measuring light induced transmission or reflection changes, in particular due to stimulated Raman emission.

BACKGROUND OF THE INVENTION

Raman spectroscopy is a well-established method to examine materials by investigating inelastic scattering of probe light. In 1928, C. V. Raman was the first who observed that intense light incident on a sample creates a wavelength shift due to inelastic scattering of light at phonons representing vibrational excitation modes of chemical bonds. The general concept of Raman scattering is explained with reference to the left half of FIG. 1. As indicated therein, an incident photon, also referred to as "pump photon" with a frequency $\omega_{pump}$ is incident on a Raman active medium and gets annihilated. The medium which was in a quantum mechanical ground state before gets excited into a vibrational or rotational state, and a scattered photon with a shifted frequency $\omega_{emission}$ is generated wherein the difference in frequency $\omega$ (or energy $\hbar\omega$) corresponds to the energy difference in the vibrational/rotational state of the medium. If the frequency of the scattered photon $\omega_{emission}$ is smaller than $\omega_{pump}$, it is called a "Stokes photon", if the frequency is higher, it is called an "anti-Stokes" photon. The frequency or wavelength shifts occurring between the incident and the emitted photons are hence indicative of the vibrational or rotational states of the medium and are consequently highly specific for different media, such as different molecules. In this regard, the Raman spectrum can be regarded as a "fingerprint" of a molecule by which it can be identified.

Raman spectrometers are used as routine analysis tools in many physics and chemistry research facilities. However, due to the small Raman scattering cross-section, pump lasers with Watt level optical output powers are usually required. Only recently, with the introduction of compact and highly efficient high power diode lasers, portable Raman spectrometers for example for drug detection have become available. However, since the Raman signal is inherently weak, for lower sample concentrations the acquisition of a single spectrum usually takes from several seconds up to minutes.

A particularly attractive application of Raman spectroscopy is the so called "Raman microscopy" or "Raman micro-spectroscopy", as for example described in G. Turrell and J. Corset, eds., *Raman microscopy developments and applications* (Academic Press, 1996). In these techniques, space resolved Raman spectra are obtained with high resolution, thereby allowing for a very powerful imaging with molecular contrast. Raman microscopy or micro-spectroscopy has been applied for imaging in inorganic and organic samples. Especially for biomedical imaging applications, there is currently a great hope that in the future Raman microscopy may be a potent biomedical imaging modality for in vitro or in vivo microscopy, providing molecular contrast without exogenous contrast agents. However, again the small Raman scattering cross-section makes Raman microscopy prohibitively slow for many applications. In practice, typically imaging protocols are chosen where only a few spectra at certain position on the sample are acquired, rather than a full high resolution en face image. An increase in imaging speed by a factor of 100 to 1000 would be highly desired.

In almost all applications, the weak Raman cross-section is the main problem of Raman spectroscopy and Raman microscopy. Even in cases where a long acquisition time is generally feasible, the small signal levels often make it difficult to identify the Raman signal on the fluorescence background. Various techniques have been proposed to increase the signal level of the detected Raman bands, such as coherent anti-Stokes Raman scattering (CARS), as for example described in A. Zumbusch, et al., "*Three-dimensional vibrational imaging by coherent anti-Stokes Raman scattering*", Physical Review Letters 82, 4142-4145 (1999) and C. L. Evans, et al., "*Chemical imaging of tissue in vivo with video-rate coherent anti-Stokes Raman scattering microscopy,*" Proc Nat Acad Sci 102, 16807-16812 (2005).

A further technique that was proposed for this purpose is the so called surface enhanced Raman scattering (SERS) as for example described in M. G. Albrecht and J. A. Creighton, "*ANOMALOUSLY INTENSE RAMAN-SPECTRA OF PYRIDINE AT A SILVER ELECTRODE,*" Journal of the American Chemical Society 99, 5215-5217 (1977). In SERS the near-field enhancement effect of the electric field in the proximity of sharp nanostructures on the sub-wavelength scale is used. Plasmonic resonances can further push the field enhancement factor which amplifies both, the electric field of the pump laser and the electric field of the scattered Raman signal. SERS can be cheap and very efficient; however, since it is based on a near-field, in most cases only substances that can be absorbed to a surface can be analyzed. In addition, SERS may provide distorted spectra due to plasmonic resonances of the field enhancing structures.

A further technique to increase the Raman signal intensity is the so called stimulated Raman scattering, which is illustrated on the right hand side of FIG. 1. In stimulated Raman scattering, besides the pump photon with frequency $\omega_{pump}$, a photon with a Stokes frequency $\omega_{probe}$ is incident on the material/probe. The Raman effect leads to an amplification of the probe signal by generating a coherent ray of Stokes photons matching the Raman probe photon. The application of a Raman probe laser greatly enhances the scattering signal but it also introduces a background signal. While stimulated Raman scattering has been known since the 1970s (A. Owyoung, "*CW STIMULATED RAMAN-SPECTROSCOPY,*" Abstracts of Papers of the American Chemical Society 175, 124-124 (1978)), the lack of low noise, widely and rapidly tunable laser sources in combination with the low signal levels impeded the widespread application.

A system for stimulated Raman spectroscopy, particularly a device for microscopy imaging systems, is described in US 2010/0046039. In this system, a first train of pulses at a first center optical frequency $\omega_1$ and a second train of pulses at a second center optical frequency $\omega_2$ are provided. The difference between $\omega_1$ and $\omega_2$ is chosen to be resonant with a specific vibrational frequency of a sample that is to be detected.

A beam property of the second train of pulses, such as its amplitude or its polarization is modulated at a frequency of at least 100 kHz. The first and second trains of pulses are directed toward a common focal volume. Downstream of the sample, the second train of pulses is blocked, and an integrated intensity of substantially all optical frequency components of the first train of pulses transmitted or reflected through the common focal volume is detected. Then, a modulation at the modulation frequency f of the integrated intensity of all optical frequency components of the first train of pulses due to the non-linear interaction of the first train of pulses with the second train of pulses in the common focal volume is provided by means of a lock-in detector, which is indicative of the degree of stimulated Raman emission. The idea of the lock-in detection is to use the modulation frequency to extract the signal from the large background of the signal of the first train of pulses itself. If $E_0$ is the intensity of the signal of the first train of pulses and $\Delta_E$ is the gain due to stimulated Raman emission, the heterodyning term $\Delta_E \cdot E_0$ can be extracted from the intensity background $E_0^2$, because it is modulated at the before mentioned modulation frequency f. By electronically filtering out all contributions of the signal except for the signal at the frequency f using a lock-in detector, it is possible to reject most of the background and to determine the contribution of stimulated emission.

Unfortunately, however, lock-in detectors are rather expensive devices. Accordingly, including the modality of this prior art in a microscope would severely increase its price.

A further major source of costs in ordinary Raman spectroscopy systems is the laser sources, where usually picosecond lasers or femtosecond lasers are employed, which are generally very costly as well.

SUMMARY OF THE INVENTION

A problem underlying the invention is to provide a system for stimulated Raman spectroscopy, or other related applications in which light induced transmission or reflection changes are detected, that allows for a comparatively simple and cost-efficient design.

This problem is solved by a system according to claim 1 and by a related method. Preferable embodiments are defined in the dependent claims.

According to the invention, the system comprises
a first light source for generating a first light signal having a first wavelength,
a second light source for generating a second light signal having a second wavelength,
an optical assembly for superposing said first and second light signals at a sample location, and
a detection means for detecting a transmitted or reflected light signal, in particular a stimulated Raman signal caused by a Raman-active medium when located at said sample location.

At least one of the first and second light sources is one of:
actively controllable to emit a time controlled light pattern or
operated substantially in CW mode and provided with an extra cavity modulation means for generating a time controlled light pattern.

Further, the detection means is capable of recording said transmitted or reflected light signal, in particular stimulated Raman signal, as a function of time.

According to the invention, at least one of the first and second light sources is controllable to emit a time controlled light pattern. This may be either achieved by using a directly controllable light source, such as a semiconductor laser diode, or by using a light source that by itself is substantially operated in CW (continuous wave) mode and provided with an extra cavity modulation means for generating the time controlled light pattern. Further, the detection means is capable of recording the transmitted or reflected light signal, in particular the stimulated Raman signal, as a function of time. As will become more apparent from the description below, by providing for the precise time control of at least one of the first and second light sources and for the time information in the detection signal, the stimulated Raman signal or related signals can be detected with good precision at significantly reduced hardware costs. Note that using the time information of the stimulated Raman signal (or related signals) allows dispensing with and can even be regarded in a sense complementary to the lock-in detection concept, where the signal is extracted based on frequency information.

Note that the term "extra cavity modulation means" distinguishes the light source from a Q-switch laser which includes a component that could be regarded as an intracavity modulator. However, with a Q-switch laser, only very limited time control is possible.

Also, the use of a controllable light source or a CW light source provided with an extra cavity modulation means differs from usual stimulated Raman spectroscopy designs employing femtosecond or picosecond lasers, which are both, very sensitive and expensive, and do not allow for an arbitrary time control.

While the detection means as such allows for a time-resolved recording of the signal, the system may further comprise processing means adapted to further process the detected transmitted or reflected signal, in particular the stimulated Raman signal, by a multiplication or convolution operation in time or frequency later on.

In a preferred embodiment, at least one of said first and second light sources is adapted for generating a time-varying first or second wavelength, respectively, such as to cause a time-dependent difference between the first and second wavelength. In a stimulated Raman emission application, one of the first and second light signals will act as pump signal and the other one as probe signal. A stimulated Raman emission will occur if the difference in wavelength (between pump signal and probe signal) matches a Raman band of a sample. With a time-varying wavelength difference, in this embodiment, the most important spectral information is therefore inherently encoded in time.

Preferably, the system comprises means for reconstructing spectral information from the time information of the time-dependent stimulated Raman signal.

Preferably, the detection means is adapted to record said transmitted or reflected light signal, in particular simulated Raman signal by means of a time-gated detection. This resembles one exemplary way of recording the signal as a function of time.

In a preferred embodiment, the first light source is a wavelength sweeping light source. In particular, the first light source may be a Fourier Domain Mode Locked (FDML) laser, a Vertical-Cavity Surface-Emitting Laser (VCSEL), a tunable external cavity semiconductor laser or a tunable Vernier diode laser. With a wavelength sweeping light source, a certain range of wavelengths and hence time-dependent differences between the first and second wavelength can be provided such that, depending on timing within the first light signal, different Stokes bands can be sampled. Further, with a wavelength sweeping light source, it is very obvious how the frequency information translates to time information. A particular advantage of using a wavelength sweeping light source is that the wavelength sweeps can be carried out at very high speeds, so that it is possible to sample different wavelengths at rapid rates. Accordingly, using wavelength sweeping light sources, it is possible to sample different Stokes bands rapidly one after the other. Further, due to the continuous wavelength change of a wavelength sweeping light source, a continuous range of wavelength differences can be sampled.

In a preferred embodiment, the first light source is adapted to carry out a periodic wavelength sweep, in particular with frequencies of at least 0.1 kHz, preferably at least 10 kHz and most preferably at least 50 kHz.

In a preferred embodiment, the first light source does not only allow fairly high sweep frequencies, but also correspondingly high sweep amplitudes, such that the actual light frequency can be tuned at considerable rates. Preferably, the first light source is capable of tuning the light frequency at a rate of more than $10^{16}$ Hz/s, preferably more than $10^{17}$ Hz/s, more preferably more than $10^{18}$ Hz/s and most preferably more than $10^{19}$ Hz/s.

In an alternative embodiment, the first light source is adapted to carry out a substantially step wise wavelength tuning, rather than a truly continuous sweep, in particular with stepping frequencies of at least 1 mHz, preferably at least 0.1 Hz and most preferably at least 1 Hz.

In an alternative embodiment, the first light source may also comprise a set of stationary narrow band lasers, preferably semiconductor laser diodes. Namely, if only a small number of different first wavelengths is desired, this is a very simple and robust way of providing the same.

Preferably, the second light source is adapted to generate modulation patterns, in particular light pulses with a predetermined timing. The second light source is preferably synchronized with the first light source such as to provide for a controlled timing of the second light source pulses with regard to the wavelength sweep of the first light source. In other words, assuming that the second light source pulses have a predetermined wavelength, still the wavelength difference between the second light source pulse and the first light signal will depend on the relative timing of the second light source pulse with regard to the wavelength sweep of the first signal. Since stimulated Raman emission only occurs when both signals are present, the timing of the second light source pulses therefore "selects" a certain first wavelength from the wavelength sweep of the first light source due to its timing. Note that the timing of the second light source pulse not only selects the "effective" wavelength from the first light signal, but it also determines the point in time at which the signal enhancement due to stimulated Raman emission may occur in the detected signal. And since the detection means is adapted to record the stimulated Raman emission as a function of time, the Raman gain within the signal at the corresponding point in time can in fact be attributed to the timing of the second light source pulse. This is one example how the system provides for relating the time information of the time-dependent Raman signal to the corresponding difference between the first and the second wavelength.

Preferably, the gap between consecutive pulses of the second light source can be chosen independently.

In a preferred embodiment, the timing of the second light source pulses with respect to the wavelength sweeps of the first light source is electronically configurable, and in particular, programmable. By electronically configuring or programming the timing of the second light source pulses with respect to the wavelength sweeps of the first light source, arbitrary wavelength differences within the interval provided by the wavelength sweep become accessible, meaning that the system allows for specifically sampling for any desired Stokes band within this range. This makes this system extremely flexible and versatile.

Preferably, the second light source is synchronized with the detector means. This provides for relating the time information of the time-dependent Raman signal to the timing of the second light source, which in some embodiments determines the time-dependent difference between the first and second wavelength. Herein, the second light source may be synchronized with one or more of a sample clock, a sample time gate, a multiplicative time trace or an acquisition trigger associated with the detection means.

Preferably, the synchronization of
the first and second light sources and/or
the second light source and the detection means
is established electronically, and in particular based on sharing common electrical signals or phase locking electrical signals involved in the time control of the respective components. The electronical synchronization of these components is one way of providing for relating the time information of the time-dependent Raman signal to the corresponding difference between the first and second wavelength. Providing for the synchronization electronically turns out to be simpler and more flexible than providing synchronization for example via the optical signals.

In a preferred embodiment, the system comprises an electronic function generator generating electronic signals for operation of one or more of the first light source, the second light source, and the detection means, and in particular, of an analogue-to-digital converter of said detection means. By using a function generator, also referred to an "all waveform generator" herein, for some or all of these components, the synchronization and the flexible programming of their timing can be easily achieved.

In a preferred embodiment, the function generator may be synchronized with or driven by the first light source. This is particularly useful if an FDML laser is used as the first light source, where the sweep frequency is related to the time required for one run of the light through the optical fiber and where this frequency may need to be adjusted during operation to account for slight deviations in optical path lengths due to temperature variations and the like.

While the function generator may be used to directly drive a modulator means for modulating one of the light sources, when it comes to generating short pulses, its time resolution may not be sufficient, or a very expensive function generator with a corresponding time resolution would have to be employed. In a preferred embodiment, a triggerable electronic pulse generator is employed which can be triggered by the function generator and which allows for generating pulses that are shorter than the time resolution of the function generator. Such pulses can for example be used for operating said extra cavity modulator.

In a preferred embodiment, a filter means for filtering the second wavelength is provided between the sample location and the detection means. This way, only the first light signal, or a portion thereof, is detected together with a possible Raman gain, if stimulated Raman emission has occurred.

In any case, the stimulated Raman emission will only be a small enhancement of the probe signal, which in this embodiment may be formed by the first signal. However, note that either one of the first and second light signals may act as the pump or probe light. Accordingly, it is necessary to in some way isolate the Raman emission from the probe light background.

In a preferred embodiment, the detection means comprises a differential photo detector. Herein, the term "differential photo detector" shall be interpreted in a broad sense and should be understood as any type of detector that may receive two light signals and determine a difference between them such as a difference in intensity or power. The photo detector can then be used to detect the difference between a measurement signal, which will include a Raman gain due to stimulated Raman emission, if present, and a reference signal, which is free of any possible stimulated Raman emission contribution.

In particular, the differential photo detector is arranged to detect a difference between
 a reference signal generated when none or only one of the first and second light signals passes the sample, and
 a measurement signal generated when both light signals pass the sample.

Only when both light signals interact with the sample (i.e. pump and probe light signals) a stimulated Raman emission may occur. If the reference light signal is generated based on the first light signal only, then the contribution of the second light signal will be filtered out in the measurement signal as well, to make the signals comparable. The same is true if the roles of the first and second signal are interchanged.

In a preferred embodiment the first light signal is split into a measurement beam and a reference beam. The measurement and reference beams may be delayed with regard to each other before reaching the sample location. This delay can then be used to provide that only the measurement beam overlaps with the second light signal, such as a pulse, but the reference beam does not. Further, downstream of the sample location, the measurement and reference beams are preferably delayed with respect to each other in a way compensating said relative delay upstream of the sample location. In other words, the reference and measurement beams, which are split from the first light signal and are hence inherently simultaneous at the beginning, are also simultaneous at the detector. Still, due to the delay, the reference and measurement beams pass the sample location at different times, and this allows to provide for an overlap with the second light signal in case of the measurement beam only.

The delays will typically be made as short as possible, while still avoiding overlap of the reference beam and the second light signal. For example, if the second light signal was a pulse with a duration of about 1 nanosecond, then a delay of a few nanoseconds would be sufficient. Even if the sample should exhibit some kind of temporal fluctuations and variations, which in fact the inventors noticed in some actual examples, these fluctuations will be slow as compared to the time scales of these delays, such that the much slower fluctuations of the sample will not lead to any differences in the measurement and reference beams.

Further, if the sample is analyzed in a transmitting mode, it is preferable that the reference beam and the measurement beam pass the sample location in different directions, preferably in opposite directions, such that the beams do not mix.

Note that in this embodiment, even if the first light source is a wavelength sweeping light source, the measurement signal and the reference signal detected at the differential detector correspond to the same wavelength and have both passed the sample, such that the difference in intensity should be attributable to the Raman gain. However, it turns out in practice that it may not be necessary to have the reference beam actually pass the sample, instead it may also be "fed around" the sample and be delivered to the differential amplifier. Also, in practice it is not always necessary that the optical path lengths of the reference and measurement signal to the differential photo detector are exactly the same, as long as the arrival times differ by less than 30 ns, preferably less than 5 ns, and most preferably less than 1 ns. Namely, even if the reference signal should be somewhat shifted with regard to the measurement signal at the differential photo detector, on these short time scales in practice the reference signal may not change too much.

On the other hand, it may happen that the first light signal is not precisely split 50:50, or that the splitting ratio may slightly depend on the wavelength. This would then lead to a difference between the measurement and reference signals that would be detected by the differential detector but that is not attributable to the Raman gain. This error can be corrected, however, by recording the differential signal without any second light signal being present, i.e. the differential signal of light from the two components of the first light signal propagating to the differential detector as reference and measurement beams as in the actual measurement but with the second light source switched off. This differential signal then reveals the effect of uneven splitting and can be used to correct the reading of the differential amplifier in the actual measurements e.g. by data processing.

In a preferred embodiment, the first light source and/or the second light source are fiber based. Herein, the expression "fiber based light source" may for example mean that at least 50%, preferably at least 75% and most preferably at least 90% of the light path within light source is located in an optical fiber.

Preferably, at least a part of one or more of the optical paths
 from the first light source to the sample location,
 from the second light source to the sample location, and/or
 from the sample location to the detection means
comprises or comprise an optical fiber. Such a fiber based design has a number of technical advantages, as it is extremely robust, and as it can be easily integrated in other imaging modalities. For example, the system according to one of the above embodiments may be part of an endoscope, an OCT device, a light microscope, a photo-acoustic imaging device or an ultrasonic imaging device, where a fiber based design turns out to be ideal. Also, a fiber based design turns out to be comparatively cheap, because the fibers themselves as well as the additional components such as couplers, WDM, line filters and the like are components that are made as mass products for the telecommunication industry with very high quality at very reasonable prices.

Preferably, the optical fiber located between the first and/or second light source and the sample location is a single-mode fiber. The optical fiber between the sample location and the detection means preferably is a multi-mode fiber. In a particularly preferred embodiment, the optical assembly comprises a dual core or double clad fiber for guiding said first and second light signals to the sample location and for guiding light from the sample location towards the detection means.

In a preferred embodiment, the optical assembly comprises means for scanning different sample locations. The means for scanning different sample locations may comprise
 one or more moving mirrors for deflecting said first and second light signals to a predetermined sample location, and/or one or more mirrors for deflecting the light reflected from the sample location, or
 a device for scanning an optical fiber or fiber bundle carrying said first and second light signals with respect to a sample, or a device for scanning the sample relative to the light signal.

Due to such scanning means, a space resolved Raman spectrum can be sampled, or simply speaking, "2D Raman images" or related images can be taken. This is particularly useful if the Raman system is combined with other types of medical or biological imaging, such as light microscopy, endoscopy or the like where the Raman spectroscopy information gives additional information about the molecular structure of the sample. Since the system of the invention can operate at very high speed, it is ideally suitable for these types of applications. Note again that the operation speed of the system of the invention is due to the inherent speed of the system itself, i.e. the very short time for sampling any given Raman band, but also due to the flexibility of this system, which enables to sample for precisely the information needed, rather than recording full spectra at each sample location. This in combination makes the system of the invention particularly suitable for scanning operations and/or 2D Raman imaging.

In a preferred embodiment, the system is operated in a mode where the first light source is periodically swept in wavelength, and the second light source generates one pulse, or two to ten pulses per sweep period of the first light source. In another preferred embodiment, the second light source is operated with a duty cycle below 60%, preferably below 2% and most preferably below 0.1%.

In a preferred embodiment, the second light source is operated with an instantaneous power on the sample location of more than 10 mW, preferably more than 10 W, and most preferably more than 400 W.

Preferably the detection means comprises an analogue-to-digital converter for digitizing the reflected or transmitted signal, in particular the stimulated Raman signal. Herein, the analogue-to-digital converter preferably digitizes the analogue signal to at least 6 bit, preferably to at least 10 bit.

In a preferred embodiment, the second light source comprises
- at least two, preferably at least three sub-light sources which are controllable by an electronic control unit,
- an interaction medium coupled with said sub-light sources such that due to interaction with the interaction medium and in response to the control of said electronic control unit, at least one of
  - an output wavelength,
  - a time dependent intensity or
  - a polarisation state
- of said second light source can be controlled.

Preferably, the second light source comprises a first sub-light source and a modulator for modulating light generated by the first sub-light source. Herein, the first sub-light source is preferably a laser light source, and in particular a semi-conductor laser light source.

In a preferred embodiment, the first sub-light source is a NIR light source having a wavelength of 900 nm to 1200 nm, and preferably a wavelength of 1000 nm to 1150 nm.

The modulator may be one of an electro-optical modulator, an acoustic-optical modulator or a swept Fabry-Pérot filter. With these types of modulators, a large variety of time-dependent amplitude modulations or, in other words, time-dependent intensities can be obtained. In particular, the modulator can preferably be electronically controlled to generate one or more of a CW light signal, a periodic sinusoidal modulation or a light pulse pattern.

In a preferred embodiment, the pulse lengths of the light pulse patterns are between 5 ps and 20 ns, preferably between 0.1 ns and 5 ns.

In a preferred embodiment, the modulator can be electronically controlled to configure the time delay between each two consecutive pulses with a mean repetition rate of 10 kHz or more, preferably 100 kHz or more and most preferably 1 MHz or more. Considering that each of the pulses allows selecting an "effective" first wavelength, this means that the Stokes band can be sampled with this high frequency, allowing for a very high detection speed.

Preferably, the second light source comprises at least one optical amplifier. The optical amplifier may for example be used to amplify the light signal generated by the first sub-light source and modulated by the aforementioned modulator.

In a preferred embodiment, the at least one optical amplifier comprises a gain medium and a second sub-light source for pumping said gain medium. The gain medium is preferably a rare-earth doped optical fiber, wherein said rare-earth is preferably one or more of Ytterbium, Erbium or Thulium.

A number of this type of optical amplifiers can be arranged in series to provide different amplification stages. Such amplifiers are also referred to as master oscillator power amplifiers (MOPAs).

In a particularly preferred embodiment, at least one of the optical amplifiers comprises a double-clad fiber having a core portion formed by a rare-earth doped single mode fiber and a cladding layer for guiding multimode pump light. In this embodiment, the core portion carries the signal to be amplified only, while the pump light is guided in the cladding layer. Accordingly, the entire light capacity of the fiber can be dedicated to the light signal to be amplified. This compares favorably with applications where both, the pump light and the light signal to be amplified are confined to the same fiber. Further, since the cladding layer allows guiding multi-mode pump light, the intensity of the pump light can be comparatively high, thereby leading to a high amplification gain.

Preferably, the pump light is fed into the cladding layer in a direction opposite to that of the light propagating in the core portion. This avoids that the amplified light signal is contaminated with pump light.

In a preferred embodiment, the second light source comprises two or more optical amplifiers, wherein between two optical amplifiers, a filter, in particular a laser line filter is provided for filtering an amplified stimulated emission background. This way the signal-to-noise ratio can be efficiently increased.

In a preferred embodiment, the second light source comprises a third sub-light source, preferably a semiconductor laser diode, for generating a Raman seed-signal, wherein said Raman seed-signal is suitable for causing a Raman wavelength shift of the light generated by said first sub-light source of the second light source. Herein, the second light source may comprise an optical fiber, in particular a silica fiber acting as the Raman active medium. The length of the fiber may be selected such as to allow for at least two consecutive Raman wavelength shifts. By employing such Raman wavelength shift, the second light source may operate at different, selectable frequencies, as will become more apparent from the specification below.

While in the introductory portion and in the previous summary mainly reference to stimulated Raman emission has been made, the system of the invention is not limited to this. Instead, the system of the invention is generally adapted for measuring light induced transmission or reflection changes that may have other causes than stimulated Raman emission. One such application is photo-acoustic imaging or photo-acoustic spectroscopy. The idea of photo-acoustic spectroscopy is to measure the effect that absorbed electromagnetic energy (particularly light) has on matter. The absorbed energy causes local heating and—through thermal expansion—pressure wave or sound. Accordingly, by analyzing the pressure waves or sound signal, the absorbing components of the sample can be identified. The set-up described above is in fact ideally suited for this.

For example, the second light source can be employed for generating a suitable second light signal, such as a pulse of a given wavelength, that is incident on the sample. If the wavelength of the second light signal should meet an absorption band of the sample, the absorbed energy leads to a local heating and hence to a pressure wave in the sample which at the same time changes the optical properties of the sample, in particular the refractive index. This will generally lead to a change of transmission or reflection of the first light signal. For example, the inventors noted that a local change in the density and hence in the refractive index of the sample caused by a shock wave due to an absorbed second light signal leads to a defocussing of the first light signal transmitted by the sample, that can be readily detected by an intensity drop.

In addition, many modifications of the first light source are likewise possible. If the first light source is a wavelength sweeping light source, the spectral sweep range can preferably be adjusted. The sweeping direction is preferably from long to short wavelengths. Further, the repetition rate, amplitude and modulation are preferably adjustable, too. In a preferred embodiment, the first light source also emits pulsed light signals, where again the pulse length, the pulse repetition rate and/or the individual intervals between consecutive pulses can be adjusted. In a preferred embodiment, both the first and second light sources may be modulated in one or more of amplitude, phase and polarization. This modulation may in particular be synchronous in phase.

In one embodiment, the pulse length of the second light source may be shorter than the gate time of an A/D converter used for data acquisition, preferably 5 times shorter and more preferably 10 times shorter. However, in alternative embodiments, the pulse length of the second light source may exceed the gate time, such as by a factor of 5 or a factor of 10.

In some embodiments, the optical assembly includes a fiber length in which measurement light and reference light propagate in opposite directions. In some embodiments, the portion of the second light signal that is filtered out before reaching the detector means is examined with regard to one or more of spectral width, time stability, local mode parameters or spectral modulation. In one embodiment, the first light signal downstream of the sample location is further processed using a heterodyne or homodyne amplification.

In various embodiments, the system may have at least one element for wavelength calibration. The system further preferably comprises means for measuring the output power of the first light source, in particular the time-dependent output power.

In some embodiments, the detector means comprises differential photo diodes with more than 15 dB common mode rejection. Preferably, at least one of the photo diodes receives more than 20 µW continuous power, preferably more than 200 µW and most preferably more than 1 mW.

In some embodiments, either one of the stimulated Raman gain or the stimulated Raman loss can be measured. For the detection, either one of a D/C coupled or A/C coupled photo detector can be employed.

In various embodiments, the electronic signal detected by the detection means is digitized. For this, an A/D converter can be used operating with a speed of >1 kilosample/s, preferably >1 megasamples/s, more preferably >100 megasamples/s and most preferably >1 gigasampies/s. The sample clock of the A/D converter can be operated in a phase-locked manner with the first and/or second light source. In one embodiment the A/D converter is triggered synchronously with the first and/or second light source. In some embodiments, an element, such as a sample-and-hold element, only detects the Raman signal amplitudes. In various embodiments, the gate time of the A/D converter is shorter than 100 ns, preferably shorter than 10 ns and most preferably shorter than 3 ns.

The A/D converter may include a sample-and-hold circuit or an integrator circuit. The A/D converter may have two synchronous inputs, where preferably two different polarization states are sampled at the two inputs.

As far as the second light source is concerned, a fast modulator based on optical filtering may be employed. Preferably, the pulse duration of pulses generated by the second light source can be adjusted variably, and in particular be programmed. Preferably, the first and/or second light signal is widened inside a fiber or a fiber coupler. Further, the second light source preferably comprises optical isolators. According to at least one embodiment, the wavelength of the second light source can be changed or different second light sources can be variably connected using wavelength-division multiplexers. Further, the Raman shift within the second light source can preferably be enhanced using an enhancement cavity, such as a Fabry-Pérot resonator or a ring resonator.

In a further preferred embodiment, the seed-light source for generating the Raman-shift seed signal can be modulated in amplitude and/or phase. In a preferred embodiment, the first sub-light source and the Raman-seed-light source can be operated in a synchronized mode. In a preferred embodiment, the pulse pattern generated by the second light source may include pulse patterns having time distances smaller than 10 ns, preferably smaller than 2 ns and most preferably smaller than 1 ns in between. This allows suppressing stimulated Brioullin-scattering efficiently. According to at least one preferred embodiment, the amplification and the Raman shift may occur simultaneously in a fiber. In various embodiments, the pulse duration of pulses generated by the second light source may be longer than 7 ps, preferably longer than 15 ps, more preferably longer than 30 ps, longer than 100 ps or longer than 800 ps. In alternative embodiments, the pulse duration is shorter than 2 ns, preferably shorter than 200 ps and most preferably shorter than 20 ps.

BRIEF DESCRIPTION OF THE FIGURES

FIG. 4 is a schematic overview of a second light source according to an embodiment of the invention FIG. 5 is a specific embodiment of a second light source according to an embodiment of the invention.

DESCRIPTION OF THE PREFERRED EMBODIMENTS

Figure 1:
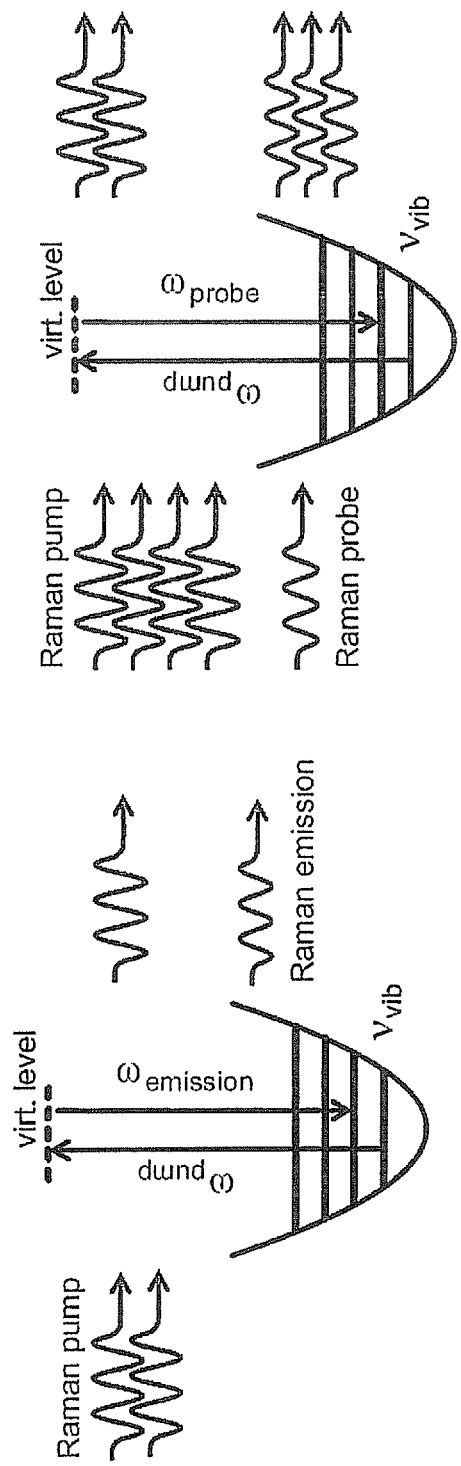
FIG. 1 shows two schematic diagrams illustrating spontaneous and stimulated Raman emission.

For the purposes of promoting an understanding of the principles of the invention, reference will now be made to the preferred embodiments illustrated in the drawings and specific language will be used to describe the same. It will nevertheless be understood that no limitation of the scope of the invention is intended thereby, such alterations and further modifications in the illustrated device and method and such further applications of the principles of the invention as illustrated therein being contemplated therein as would normally occur now or in the future to one skilled in the art to which the invention relates.

Figure 2:
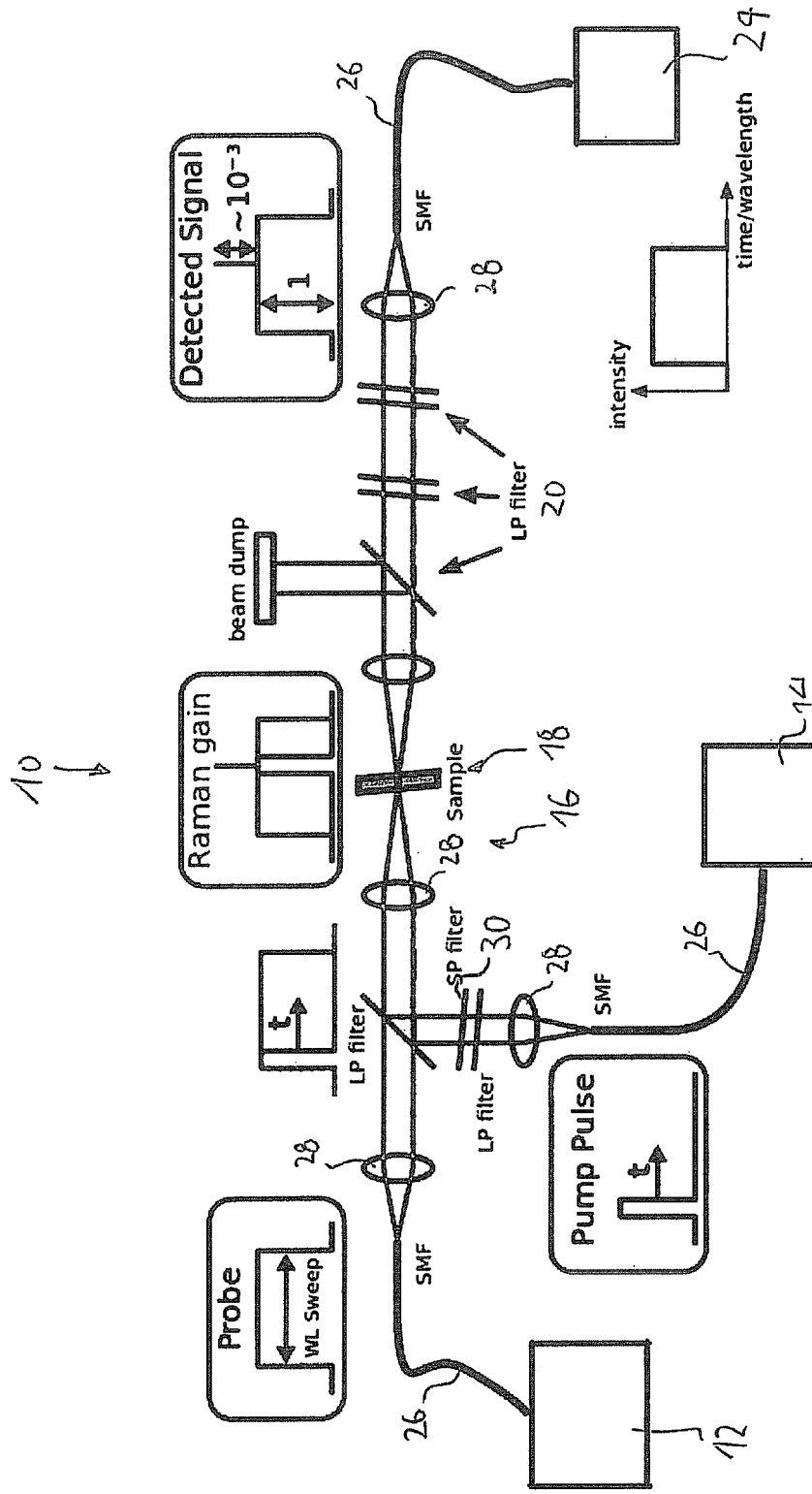
FIG. 2 is a schematic overview of a system for measuring light induced transmission or reflection changes, in particular due to stimulated Raman emission according to an embodiment of the invention.

FIG. 2 is a schematic overview of a system 10 for stimulated Raman spectroscopy according to an embodiment of the present invention. The system 10 comprises a first light source 12 for generating a first light signal having a first wavelength and a second light source 14 for generating a second light signal having a second wavelength. In the present example, the first light source 12 is a wavelength sweeping light source, which is adapted to carry out periodical wavelength sweeps. In the present setup, the first light source 12 acts as the probe signal in the stimulated Raman scattering described in more detail below.

The second light source 14 is a light source for generating short light pulses having a duration of a few nanoseconds and a power of several kW. In the present setup, the second light source acts as the pump source for the stimulated Raman scattering. However, in a modified setup the role of pump and probe sources could be reversed.

The system 10 further comprises an optical assembly generally shown at reference sign 16 which is adapted to superpose the first and second light signals, i.e. the probe and pump light signals at a sample location 18. In the general mode of operation, the second light source 14 emits a series of pulses having a constant wavelength but a precisely controlled timing with respect to the swept wavelength probe signal generated by the first light source 12. Depending on the relative timing of these pump pulses with regard to the swept frequency probe signals, corresponding wavelength differences between the pump and the probe signals at the sample location 18 may occur, or in other words, different Stokes bands can be detected by stimulated Raman emission. Since the probe signal can only cause a stimulated Raman signal while the pump signal is present, the short fraction of the swept probe signal that overlaps in time with the pump signal pulse can therefore be regarded as the "effective probe signal", and the frequency of the "effective" probe signal is determined by the timing of the pump pulse which, simply speaking, "selects" an effective wavelength from the wavelength sweep of the first light source 12.

Downstream of the sample location 18, the pump light, i.e. the shorter wavelength light, is filtered using optical long pass filters 20 and directed to a beam dump 22 to avoid detrimental scattering. Only the probe light, together with the stimulated Raman signal which enhances the "effective wavelength" portion of the probe signal by what is referred to in FIG. 2 as the "Raman gain" is directed to a detection means 24 described in more detail below as well. The detection means 24 is adapted to detect the stimulated Raman signal as a function of time, and it is likewise synchronized with the first and second light sources 12, 14. The time information of the time dependent simulated Raman signal is hence related to the relative timing of the pump pulse and the wavelength swept probe pulse or, in other words, the difference between the pump wavelength and the "effective" probe wavelength. Accordingly, the spectral information of the Raman signal is encoded in the time information of the stimulated Raman signal detected at the detection means 24.

As is seen from FIG. 2, the optical assembly 16 is based on single mode optical fibers (SMF) 26 to a good part. An additional bulk optics part of the optical assembly 16 involves lenses 28, long pass filters 20 and a short pass filter 30 and is provided near the sample location 18. Noting that FIG. 2 is of course not drawn to scale, the skilled person will appreciate that in fact most of the light path is accommodated in optical fibers 26, or in other words, that the optical assembly 16 is to a good part fiber based. Also, as will be described in more detail below, in the preferred embodiments both the first and second light sources 12, 14 are fiber based as well. Accordingly, the design of the system 10 is mainly based on fiber optics, which allows for a very compact and robust design, and allows to resort to comparatively cheap components available from the telecommunication industry. Further, due to the fiber based setup, the system 10 is ideally suited for combining with or integrating into other imaging or analysis equipment, such as an endoscope, an OCT device, a light microscope, a photo-acoustic imaging device or an ultrasonic imaging device.

After giving an overview of the system 10 with reference to FIG. 2, in the following, the main components of the system will be described in more detail.

1. First Light Source

Figure 3:
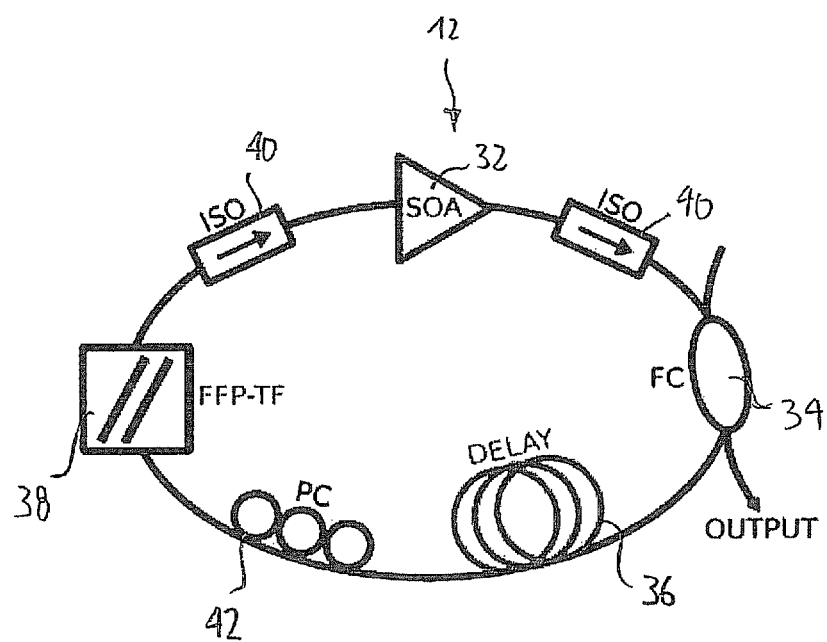
FIG. 3 is a schematic overview of a Fourier domain mode locked laser.

The first light source 12 of the system 10 of the invention is a wavelength sweeping light source. In the presently preferred embodiment, the first light source 12 is a Fourier domain mode locked (FDML) laser. FDML lasers have first been described in R. Huber, M Wojtkowski, and J. G. Fujimoto. *Fourier Domain Mode Locking* (*FDML*): *A new laser operating regime and applications for optical coherence tomography.* Optics Express, 14(8):3225-3237, 2006. The typcial structure of an FDML laser is shown in FIG. 3. The FDML laser comprises a semiconductor optical amplifier 32, a fiber coupler 34 for tapping the output signal, a fiber delay loop 36 having a length of the order of 1 km and a fiber Fabry-Pérot tunable filter 38. The FDML laser shown in FIG. 3 further includes optical isolators 40 and a polarization controller 42.

The general idea of an FDML laser is to incorporate a dispersion managed delay in the resonator by the delay fiber 36 and driving the fiber Fabry-Pérot tunable filter 38 periodically with the inverse round-trip time of the light through the total fiber assembly shown in FIG. 3. Accordingly, light with a certain wavelength passes through the loop and arrives at the filter 38 at exactly the time when the filter has the same transmission window again. This means that the filter does not dissipate any energy as, ideally, no light is actually filtered away and there is always light at the specific wavelength passing by the filter to induce stimulated emission in the gain media.

A practical advantage of using an FDML laser for the first light source 12 (probe light source in the system of FIG. 2) is that it is comparatively cheap and robust since it is to the main part fiber based, and at the same time allows for very fast wavelength scans which are only limited by the operation frequency of the fiber Fabry-Pérot tunable filter (FFP-TF) 38. One of the present inventors has recently proposed FFP-TFs which allow for wavelength scan frequencies of several hundreds of kHz and even beyond 1 MHz, see EP 12 180 271.

2. Second Light Source

Since the intensity of the stimulated Raman signal is proportional to the pump power, the second light source 14 should preferably be a light source that can generate strong pump light pulses having peak powers of e.g. several kW. Further, since the wavelength difference between the pump pulse and the "effective probe signal" depends on the current timing of the pump pulse with regard to the wavelength sweep of the probe signal, the second light source 14 calls for a precise and flexible control of the output light pattern.

To meet these requirements, in the preferred embodiments the present disclosure makes use of a general structure summarized in FIG. 4. According to this structure, the second light source 14 comprises at least two, preferably at least three sub-light sources 44 which are controllable by an electronic control unit 46. The sub-light sources 44 are coupled with an interaction medium 48. In response to the interaction of the light from the sub-light sources 44 with the interaction medium 48 and with each other, and in response to the control of the electronic control unit 46, the output wavelength Δ(a), the time-dependent intensity I(b) and a polarization state p(c) of the light output 49 can be controlled. Herein, the precisely timed pump pulse pattern referred to above is an example of the controllable "time-dependent intensity" I(b).

With reference to FIG. 5, a more specific example of the second light source 14 is shown. Herein, corresponding components are designated with the same reference signs as in FIG. 4.

In FIG. 5, a narrowband laser light source 44*a* generates an initial light signal, under the control of the electronic control unit 46. More precisely, the control unit 46 controls a suitable modulator (not shown) such as to arbitrarily modulate the amplitude and/or phase of the first sub-light source 44*a*. The modulated light signal of the first sub-light source 44*a* is then amplified in an amplifier 50 having a gain medium that is pumped by a second sub-light source 44*b*. The gain medium is an example of the "interaction medium" 48 referred to with reference to FIG. 4 above. Consequently, the "interaction medium" 48 is also designated in FIG. 5 by the dashed box. While only one amplifier 50 is shown in FIG. 5, a plurality of amplifiers 50 can be arranged in series to thereby amplify the modulated output signal of the first auxiliary light source 44*a*.

With further reference to FIG. 5, the modulated and amplified output signal can be shifted in wavelength using stimulated Raman emission. For this, a third sub-light source 44*c* generates a Raman shift seed-signal that is also fed into a portion of the interaction medium 48, such as an optical fiber. For this purpose, in the example of FIG. 5 a wavelength division multiplexer 52 is used. The Raman shift seed-signal generated by the third sub-light source 44*c* differs from the wavelength of the initial light signal generated by the first sub-light source 44*a* by a Stokes band of a Raman active medium, which is also a part of the "interaction medium" 48. The purpose of the Raman shift seed-signal is to induce stimulated Raman emission in a portion of the interaction medium 48 to thereby generate a Raman-shifted output signal. For example, if the interaction medium 48 comprises a silica fiber of the type often used in telecommunication applications, a very intense signal can act as a pump source for a spontaneous Raman effect in the fiber. The strong narrow band pump signal would then usually be shifted towards a broad spectrum having a maximum intensity shift by 13 to 15 THz with respect to the pump signal. Using the Raman shift seed-signal generated by the third sub-light source 44*c*, however, a stimulated emission is caused, and the broad spectrum known from the spontaneous Raman effect will be reduced to a narrow peak having the spectral properties of the Raman seed-signal.

Note that stimulated Raman scattering in an optical fiber only occurs in a significant amount when high powers are applied. For this, a second amplifier 54 is provided which likewise comprises a gain medium and is pumped by a forth sub-light source 44*d*. The inventors have, however, found out that it is advantageous to actually feed in the Raman shift seed-signal prior to the last amplification stage 54. Namely, as long as the intensity of the original light signal as generated by the first sub-light source 44*a* and preamplified by the amplifier 50 is still low, the Raman gain is negligible, such that bringing in the seed-signal does not have any significant impact on the light. Only when the original light receives a strong amplification in the second amplifier 54, the broad band Raman gain is seeded by the narrow Raman seed. In total this leads to a narrow line width at the shifted wavelength, where the pulse properties of the initial signal generated by the first sub-light source 44*a* can largely be conserved. In particular, this allows avoiding a parasitic Raman background in the spectrum.

With further reference to FIG. 5, downstream of the second amplifier 54, an optical fiber 56 is shown which may act as the Raman active medium for the intended wavelength shift. Based on the length of the optical fiber 56, the Raman shift can be repeated in the sense that two or more Raman shifts may occur in sequence, thereby allowing for another one or even more wavelength shifts. The optical fiber 56 can also be split in different fibers of different lengths to generate outputs with different wavelength shifts due to a different number of consecutive Raman shifts.

The third sub-light source 44c may be a tunable laser light source, for example a grating based tunable light source or a Fabry-Pérot tunable laser. One or all of the sub-light sources 44a to 44d may have a polarization analyzer or other polarization control means. This is particularly important for the third sub-light source 44c, because the Raman gain strongly depends on the polarization of pump and Stokes light. It is maximal for parallel and minimal for orthogonal polarization. Since there are birefringence fracturations in the fiber, the polarization of the Stokes and pump light will change for each wavelength differently during propagation in the fiber. This will lead to different gains if different stress or strain is applied to the fiber or if temperature changes are present, as these effects have an impact of the birefringence of the fiber. To be able to optimize the polarization in terms of the above mentioned impacts, a polarization analyzer or polarization controller is preferably used in the generation of the Raman shift seed light.

The wavelength of the first sub-light source 44a is preferably between 1044 and 1084 nm, preferably between 1054 and 1074 nm, because this allows for a compatibility with most YAG laser optics. In an alternative embodiment, the output wavelength of the first sub-light source 44a is between 1010 and 1050 nm, more preferably between 1020 and 1040 nm, because this allows for a maximum amplification using Ytterbium as the gain medium, which is a preferred material for this purpose. In yet an alternative embodiment, the wavelength of the first sub-light source 44a is in the range of 950 to 1050 nm, preferably 980 to 1020 nm, to allow for a maximum Raman shift.

Preferably, the wavelength of the Raman shift seed signal is redshifted as compared to the wavelength of the first sub-light source 44a by 300 to 700 $cm^{-2}$, preferably by 400 to 600 $cm^{-1}$.

Figure 6:
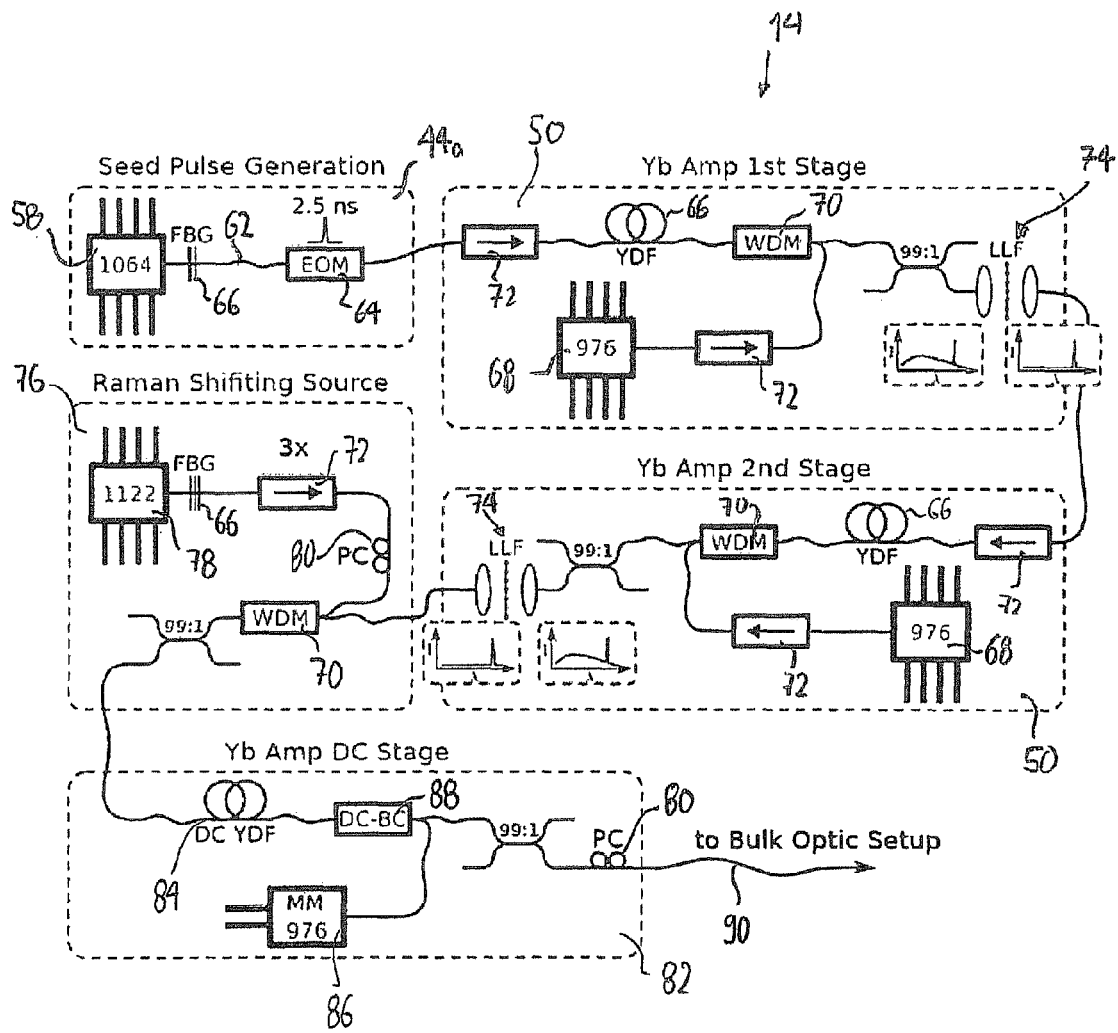
FIG. 6 is a diagram showing a specific embodiment of the second light source of FIG. 5, FIGS. 7 and 8 are multiple Raman spectra of the second light source of FIG. 6.

With reference to FIG. 6, a specific embodiment of the second light source 14 according to FIG. 5 is shown. Again, corresponding components are designated with identical reference signs.

As shown in FIG. 6, a first sub-light source 44a is provided for generating a seed light pulse. The first sub-light source 44a comprises a 1064 nm laser diode 58 with a fiber Bragg grating 60. The laser diode 58 is connected via a polarization maintaining fiber 62 to an electro optical modulator 64 which modulates the light signal from the laser diode 58 to generate pulses with a duration of 2.5 ns at desired timing, under control of a control unit like the control unit 46 of FIGS. 4 and 5, which is not shown in FIG. 6. Actually, the electro optical modulator 64 would allow for shorter light pulses, as short as 100 ps only. A short pulse would at first sight be desirable because the shorter the pulse, the higher the maximum pumping power and hence the higher the Raman signal. However, as the Raman signal length is as long as the pump pulse, the detection electronics has to be able to detect correspondingly short signals. A very good compromise between high peak power and good signal detection for the set up tested by the inventors turned out to be 2.0 to 3.0 ns, but future solutions may tend towards shorter pulses.

Downstream of the first sub-light source 44a, a first amplification stage 50 is provided. The first amplification stage 50 comprises an Ytterbium doped fiber 66 as a gain material which is pumped by a 976 nm laser diode 68. The pump light is coupled into the Ytterbium doped fiber 66 by means of a wave division multiplexer (WDM) 70. In the optical fibers, isolators 72 are further provided. The length of the Ytterbium doped optical fiber 66 is chosen to yield a good compromise between gain and amplified stimulated emission (ASE). A preferable length of the Ytterbium doped fiber 66 is between 1.5 and 2.5 meters.

The thus amplified light signal is fed through a laser line filter 74 into a second amplification stage 50 which is generally the same as the first amplification stage 50 and therefore need not be described again.

The laser line filter 74 serves to filter the ASE background, as is apparent from the illustrative boxes shown in FIG. 6. Instead of laser line filters, other filter designs can be used.

The Raman shifting source 76 is provided for generating a Raman shift seed signal. The Raman shifting source 76 comprises a 1122 nm laser diode 78 which may be selectively turned on or off under control of a control unit (not shown), depending on whether a Raman shift of the output light is intended or not. Light from the 1122 nm laser diode 78 is fed through a polarization controller 80 allowing to adjust the polarization of the Raman shift seed signal such as to cause an optimum stimulated Raman emission. The polarization adjusted light from the 1122 nm light source 78 is coupled into the 1064 nm light pulse signal that was shaped by the electro optical modulator 64 and amplified in the two amplification stages 50 via another WDM 70. Both, the 1122 nm Raman shift seed signal and the pre-amplified 1064 nm pulse are fed into a final amplification stage 82 which is also referred to as a double clad (DC) amplification stage also schematically shown in FIG. 6. A double clad fiber usually consists of three layers of material, namely a core, a first cladding and a second cladding. With a decreasing refractive index from core to second cladding, light can be guided in the core and in the first cladding, respectively. The final amplification stage 82 comprises a double cladding fiber 84 having a single-mode Ytterbium doped core and a first cladding, to which 956 nm pump light generated by a 976 nm multimode pump source 86 is fed via a double clad-beam combiner 88. Since multi-mode pump light is fed into the first cladding of the double cladding fiber 84, a very strong amplification can be generated. Namely, using a multimode diode 86 higher intensities can be achieved as compared to a single mode diode. Also, while in the first and second amplification stages 50 the single-mode Ytterbium doped fibers 66 need to carry both, the signal as well as the pump light, in the double clad fiber 84 of the final amplification stage 82, the Ytterbium doped core fiber is reserved for the signal only, such that the full capacity thereof can be used for the signal. As seen in FIG. 6, the multimode pump light is directed in opposite direction to the propagation direction of the signal within the core of the double clad fiber 84 such that the pump light will not contaminate the amplified 1064 nm light.

When the laser diode 78 of the Raman shifting source 76 is turned off, the final amplification stage 82 simply amplifies the 1064 nm pulse. However, if the Raman shifting source 76 is turned on, the light of the Raman shifting source 76 acts as a stimulated Raman emission seed signal within a fiber 90 leading to the bulk optic setup or, in other words, the sample location 18 (not shown in FIG. 6).

Figure 7:
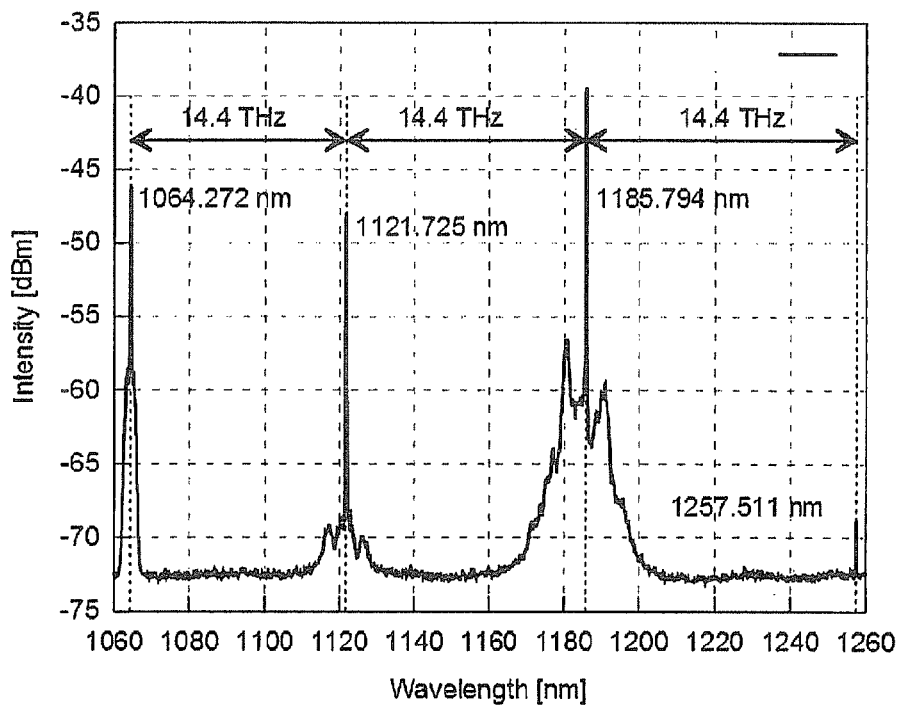

FIG. 7 shows the spectrum of the light obtained in the fiber 90 of FIG. 6, if the Raman shifting source 76 is turned on. As is shown in FIG. 7, a spectrally narrow 1064 nm (i.e.

non-shifted) spectral peak is obtained, as is to be expected. Further, a peak at about 1122 nm (1121.725 nm) is observed which is due to the stimulated Raman emission with a Raman seed signal of this wavelength. The frequency shift between these two signals is 14.4 THz, as is also indicated in FIG. 7, which corresponds to a Stokes band of the silica material constituting the fiber 90. Further note that an additional peak is present at about 1185 nm (1185.794 nm), i.e. at a further frequency shift of 14.4 THz. This peak is again very narrow, although no corresponding Raman seed signal is applied. A fourth, but smaller peak is seen at about 1257 nm (1257.511 nm). Further, FIG. 8 shows a close-up of the spectrum of the non-shifted peak at 1064 nm and the Raman shifted peak at 1122 nm.

Figure 8:
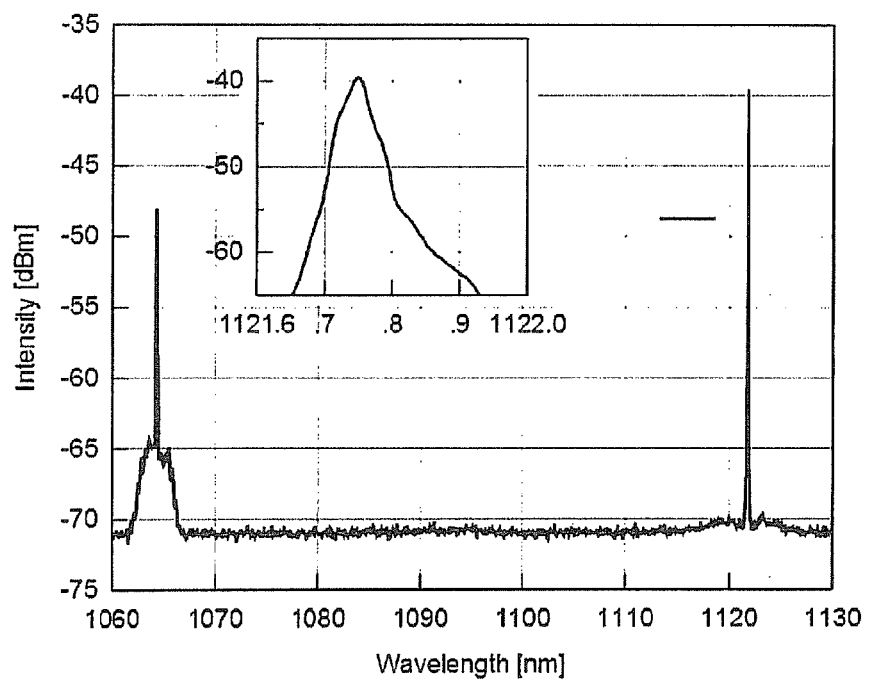

As is seen from FIGS. 7 and 8, using the stimulated Raman emission, narrow wavelength signals at different wavelengths can be generated, where the frequency shift depends on the Raman shift seed signal and can therefore to some extent be adjusted by the design. It is also found that the timing and the pulse shape of the amplified and Raman shifted signal are still very similar to the seed pulse prior to amplification, i.e. as modulated by the electro optical modulator 64. Accordingly, the second light source 14 allows generating light signals of practically arbitrary shape, owing to the modulation by the electro optical modulator 64, with very strong amplification as effected by the first and second amplification stages 50 and the final amplification stage 82, and with an optional frequency shift by one or more consecutive or combined Raman shifts.

This second light source 14 as shown in FIG. 6 is hence ideally suited for the system 10 of FIG. 2, because it allows
- generating short light pulses at precisely electronically configurable, programmable timings,
- generating very high peak powers of several kilowatts and
- for optional frequency shifts, which in combination with the frequency sweeps of the first light source 12 (see FIG. 2) allows covering a very large range of Stokes frequencies.

As was explained with reference to FIG. 5 above, the number of repeated Raman shifts arising will depend on the length of the fiber 90. Accordingly, the desired wavelength shift can be controlled by the length of the fiber 90. In some embodiments, fibers 90 with different lengths can be attached, giving rise to the desired number of consecutive Raman shifts, or, in other words, the desired output wavelength. It is also possible to permanently attach a short fiber (for 1122 nm light) and a longer fiber (for 1185 nm light) using a suitable coupler, and get longer fibers 90 for even longer wavelengths.

In one embodiment, the amplification and Raman shift occur simultaneously in the same optical fiber. In one embodiment, a tunable light source is used for generating the Raman shift seed signal, which in turn allows choosing the wavelength obtainable by the multiple stimulated Raman shifts. For this, for example, a grating based tunable laser or a Fabry-Pérot tunable laser can be used. While in case of the repeated Raman shift several frequencies of output light are usually generated, the selection of these suitable wavelengths can be chosen using suitable filters at the or close to the sample location 18. In some embodiments, the selection of the appropriate wavelengths can be achieved using a fiber Bragg grating which is connected via a circulator. It is, however, also possible to select the wavelengths using optical filters in the fiber setup.

In some embodiments, the modulator 64 is an electro optical modulator having a switch voltage of <40 Volt, preferably <10 Volt and most preferably <5.6 Volt.

In some embodiments, the seed signal is modulated, by means of the EOM 64, with a frequency of more than 200 MHz, preferably more than 500 MHz, more preferably more than 1 GHz, more than 2.5 GHz or 10 GHz, with regard to either one of amplitude or phase.

Moreover, some of the fibers used in the second light source 14 may be polarization conserving fibers. In particular, the fibers may be single-mode fibers of the group SMF28 or its equivalents or Hi1060 or its equivalents.

3. Detection Setup

In the preferred embodiment, the stimulated Raman emission signal is measured using a differential photo detector. The idea is to detect the difference between
- a light signal generated when none or only one of the first and second light signals interacts with the sample, and
- a light signal generated when both light signals interact with the sample.

The difference in these signals can then be attributed, at least in part, to the stimulated Raman emission.

In the system 10 shown in FIG. 2, the pump light generated by the second light source 14 is blocked by long pass filters 20 while the swept frequency probe light signal generated by the first light source 12 is passed to the detector. If the overlap of the pump pulse and the swept probe signal at the sample location 18 should lead to stimulated Raman emission, the probe signal is slightly enhanced thereby which is also referred to as "Raman gain" herein. However, this Raman gain is about three orders of magnitude smaller than the pump signal itself, such that this Raman gain is not easy to detect with good precision. For this, the above mentioned detection using a differential photo detector is particularly useful.

Figure 9:
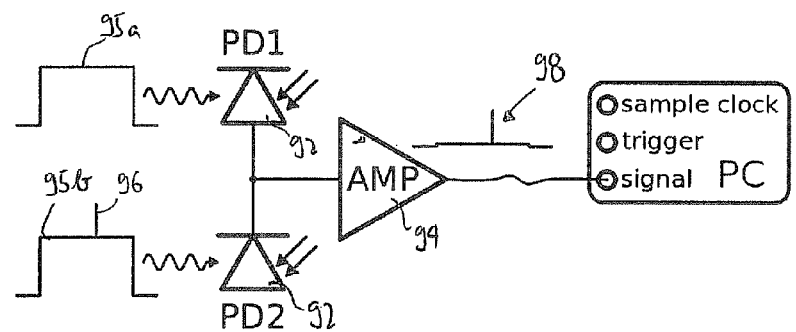
FIG. 9 is a schematic overview of a differential detection scheme.

FIG. 9 shows a specific example of the detection scheme. The detector comprises two photo detectors such as photo diodes 92 and an amplifier 94. The amplifier 94 detects and amplifies the difference in the signals outputted by the photo diodes 92.

In FIG. 9, the upper diode receives the probe signal 95a from the sample location 18 without a pump signal present (or along a path avoiding the sample location altogether). The lower photo diode 92 receives the probe signal 95b in a situation, where a pump pulse is present and the wavelength difference between the pump pulse and the "effective" probe wavelength corresponds to a Stokes band, i.e. when stimulated Raman emission occurs. This leads to a Raman gain illustrated as a spike 96 in the lower signal of FIG. 9, which is shown with a largely exaggerated amplitude.

Then, the output of the amplifier 94 would resemble only the Raman gain and hence a signal that is indicative of a stimulated Raman emission, as shown at 98 in FIG. 9.

Figure 10:
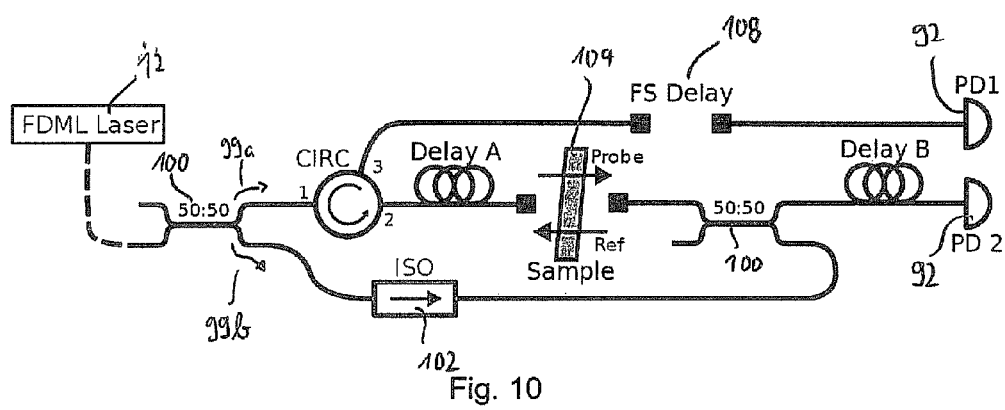
FIG. 10 is a schematic overview of a balanced detection scheme.

In applying the differential or balanced measuring scheme of FIG. 9, the inventors noticed that in practice the signal quality can be poor due to intensity variations in the signal caused by some attenuation or scattering in the sample. It turned out that in some cases, the balanced signal was even dominated by such a parasitic effect. In order to overcome this drawback, an advanced balancing scheme was implemented as shown in FIG. 10. The underlying idea is that the fluctuations in the sample vary slowly in time and should not be apparent if the measurement beam, i.e. the beam where pump and probe signals overlap, and the reference beam, where no pump signal is applied, pass the sample with a very small time delay only, such that the fluctuations would affect both, the measuring signal and the reference signal in much the same way. In the advanced balancing scheme of FIG. 10, the probe signal generated by the first light source 12 is split up into a measurement beam 99a and a reference beam 99b by means of a 50:50 coupler 100. The reference beam 99b passes an optical isolator 102 and another 50:50 coupler 100 before entering the bulk optic setup. It propagates through a sample 104, however in backward direction compared to the measurement light. It is then again coupled into a fiber, passes a fiber delay A and enters a circulator 106 at port 2, where it is directed via a port 3 to a free space delay line 108 and a detection photo diode 92.

The measurement beam 99a, on the other hand, enters the circulator 106 at port 1 and is directed via port 2 into the fiber delay A. The delay is chosen to retard the probe beam by about 10 ns compared to the reference beam when both are entering the sample 104. After going through the sample 104, the measurement signal also passes the 50:50 coupler 100 and enters fiber delay B. This delay, in combination with the free space delay 108 for fine tuning, is to compensate the time difference of the measurement and reference signals to have both incident on the photo diodes 92 simultaneously.

As is seen from the setup in FIG. 10, the measurement signal and the reference signal pass the sample 104 with only minimum delay, which means that any fluctuations in intensity due to the sample 104 should cancel out, as long as they are slowly varying as compared to the delay. The inventors found that with this advanced balancing scheme, the signal quality could be greatly improved.

While in the advanced balancing scheme of FIG. 10 the reference signal is also guided through the sample 104, in practice this is not always necessary. Instead, it may be sufficient to feed the sample beam 99b around the sample altogether and to this way use 50% of the probe light as the reference signal.

Further, the detection scheme is based on the assumption that, in absence of stimulated Raman emission, the reference signal and measurement signals are identical. However, in practice this need not always be the case. In fact, if the splitter 100 should not precisely split the light signals in equal amounts, this would lead to a differential signal in the amplifier 94. In fact, a precise splitting is not always possible over the entire wavelength range, since the splitting ratio may be slightly wavelength dependent. In order to distinguish a differential signal due to Raman emission and due to other causes, in a preferred embodiment a differential signal is recorded in a situation where there is no pump pulse altogether, in an additional measurement, preferably at the same wavelength. This can for example be done in the previous wavelength sweep, or it can be done in the same wavelength sweep shortly before or shortly after the pump pulse, under the justified assumption that the difference will not change much. Then, this difference can be used to digitally correct the differential signal, typically in the computer (not shown), e.g. by subtracting the two differential signals from each other.

Figure 11:
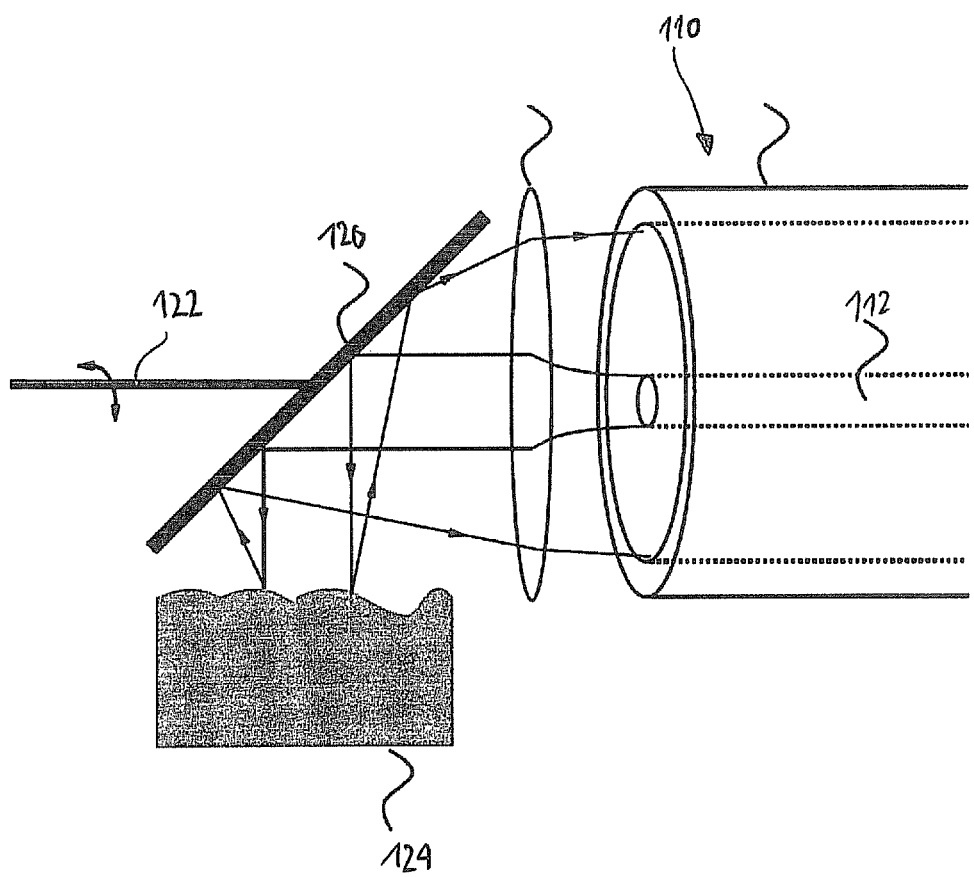
FIG. 11 is an embodiment of a fiber based system including a movable mirror for scanning a sample.

In FIGS. 2 and 10, the sample 104 at the sample location 18 is analyzed in a transmissive mode. For example, the sample 104 could be a container or a flow cell or the like including a medium to be analyzed. However, the system 10 is by no means limited to this and can instead also be operated in a reflective mode. An example for this is shown in FIG. 11, where the system 10 is adapted for use in an endoscope or the like. In FIG. 11, a double clad fiber 110 is used including a fiber core, preferably a single-mode fiber core 112, a first cladding layer 114 and a second cladding layer 116. Both, pump and probe light are delivered through the core fiber 112 and collimated by means of a lens 118 onto a moveable mirror 120. The moveable mirror 120 can be rotated around an axis 122, thereby scanning the pump and probe light over a sample 124. Herein, the mirror 120 can be moved either using an electric motor or magnetic actuation. Reflected light, including a possible Raman gain, is then reflected, at least in part, into the first cladding layer 114 of the double-clad fiber 110, which acts as a multi-mode fiber, and guided towards the detection means (not shown in FIG. 11).

FIG. 11 illustrates how the entire setup is ideally suitable for integration into an endoscopic device. Also, by scanning different points of the sample, a truly 2D "Raman image" can be obtained. Herein, the "Raman image" shall mean that from any point covered in the scan, the desired Raman information can be obtained. For example, for each scanned point, a predetermined number of Raman bands can be sampled for, by adjusting the difference in pump and ("effective") probe wavelength by means of the proper timing of the pump pulse with respect to the swept probe signal. Since the Raman band to be sampled for can be adjusted at will, under electronic control of the timing of the pump pulse, one predetermined Raman band can be sampled for every sweep of the probe signal. By using several pump pulses per wavelength sweep of the first source, the data acquisition rate can even be multiplied. With the thus achievable sampling speed, 2D Raman imaging becomes truly affordable.

4. Data Acquisition and Synchronization

As is apparent from the previous description, the system 10 relies on a precise and correct time synchronization between the electronic components involved. In the preferred embodiment, the reference signals for all electronic devices are generated by a function generator, also referred to as "all waveform generator" (AWG) 126 shown in FIG. 12. The all waveform generator 126 can be phase-locked onto a master frequency and the output can be controlled by arbitrary waveforms. In the present setup, the master frequency is determined by the FDML laser 128, because a driving frequency for the fiber Fabry-Pérot tunable filter (FFP-TF) 38 is given by the round trip time of the laser itself, see FIG. 3. Since the optical path length, which involves on the order of one kilometer of optical fiber, may vary due to temperature fluctuations and the like, it may be necessary to slightly adjust the sweep frequency during operation to obtain optimum output at the FDML laser 128. Accordingly, for this reason it is advantageous to use the operation frequency of the FDML laser 128 as the master frequency.

Figure 12:
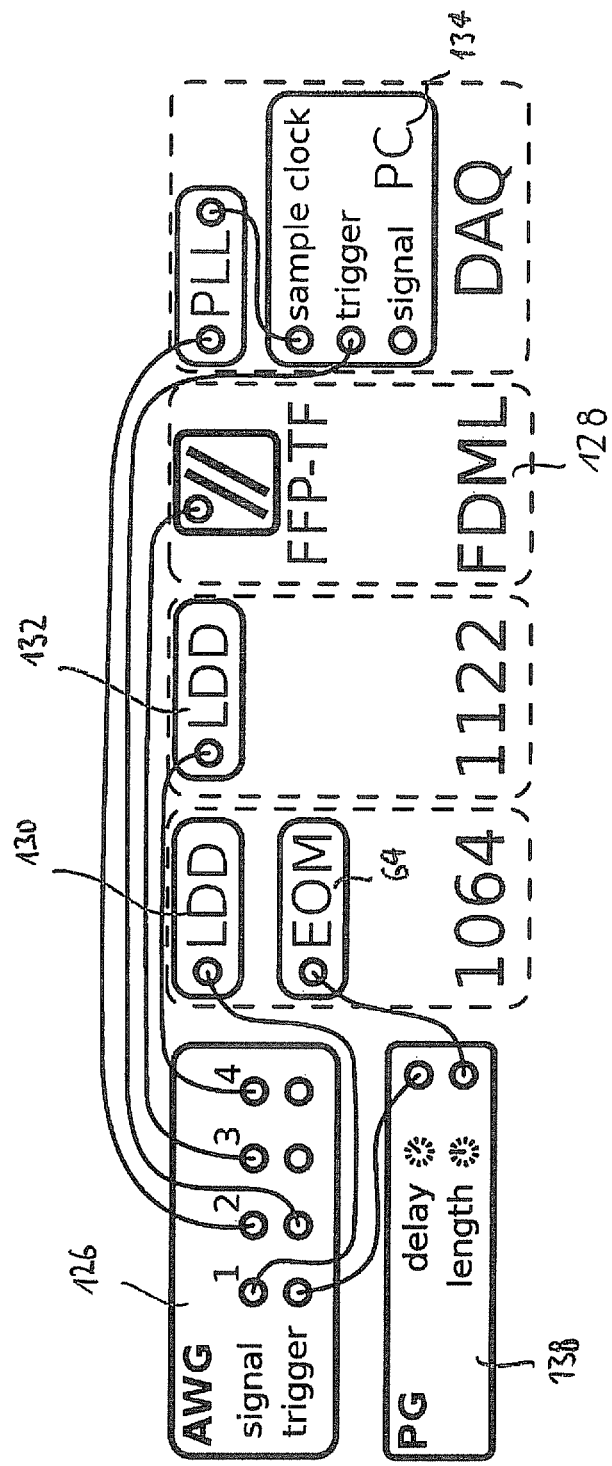
FIG. 12 is a schematic overview of different electrical components and how they are electronically synchronized.

In the setup of FIG. 12, the six components are controlled by the AWG 126, namely a laser diode driver 130 for the 1064 nm diode 58 of the second light source 14, the electro optic modulator 64 (see FIG. 6) for generating the pump pulses, another laser diode driver 132 for driving the 1122 nm diode 78 for generating the Raman shift seed signal, the Fabry-Pérot tunable filter 38 for the FDML laser 128 and a data acquisition card 134 in a personal computer in combination with a phase locked loop 136. Note that in FIG. 12, the electro optical modulator 64 is not directly driven by the AWG 126 but by a triggerable pulse generator 138, as the AWG 126 cannot produce sufficiently short electrical pulses. By means of the pulse generator 138, the pulse length and the delay can be adjusted, where the trigger for the pulses is received from the AWG 126.

Figure 13:
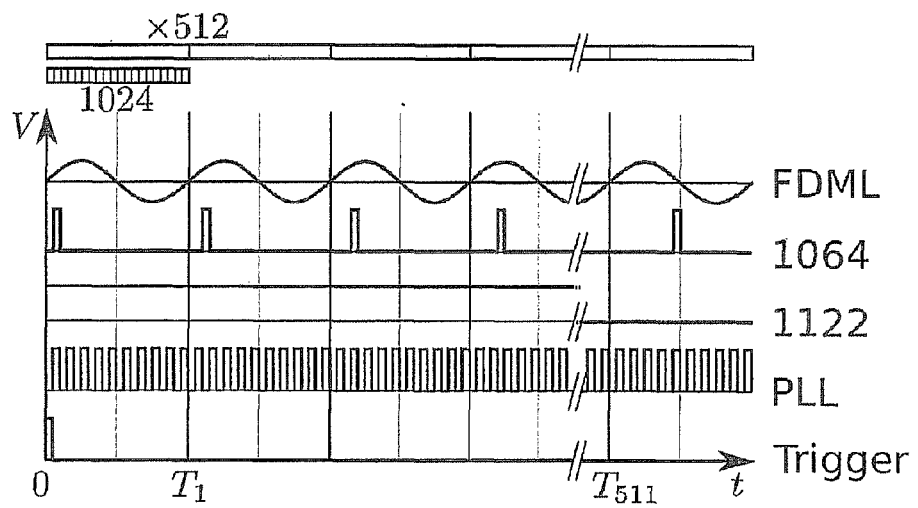
FIG. 13 is a diagram showing the relative timing of the various components of the system.

The synchronization of the different channels of the AWG shown in FIG. 12 is further illustrated in FIG. 13. In the specific example, the wave forms are generated from several lengths of 1024×512 samples. As is seen in FIG. 13, the waveform of the FDML laser is a sine. The second depicted waveform is for the 1064 nm laser diode modulation. As is seen in FIG. 13, the modulation amounts to short pulses which, after amplification in the first and second amplification stages 50 and the final amplification stage 82 of FIG. 6 and a possible frequency shift due to stimulated Raman emission, leads to the pulsed pump signals. As is further seen in FIG. 13, the relative timing of the 1064 nm pulses with regard to the frequency sweeps of the FDML laser amounts to a selection of "effective probe wavelengths" and hence frequency differences corresponding to possible Stokes bands.

With further reference to FIG. 13, the 1122 nm pulse is constantly on, i.e. operating in a CW mode. This is the case when a Raman shift in the signal is desired, i.e. if pump wavelengths of 1122 nm or 1185 nm are desired. If pump pulses of 1064 nm should be desired, the 1122 nm Raman shift seed signal would simply be off.

The last two channels are for data acquisition. The PLL multiplies its input frequency to a desired frequency and can be used for the sample clock of the data acquisition card 134, which is synchronized with a FDML laser frequency and the pump pulses. The last channel of the waveform generator is a trigger for data recording at the beginning of each sequence.

Note that in the system 10 described above, all frequency information is encoded in time. That is to say, the frequency difference of the pump signal and the "effective" probe signal are determined by the timing of the pump pulse of the second light source 14 with regard to the frequency sweep of the first light source 12. Also, the frequency information of the Raman gain is encoded in the time information in the time-dependent stimulated Raman signal. Since the timing of the pump pulses with regard to the probe signals can be electronically configured or programmed at will, the spectral information can be obtained as needed. This means that, instead of recording an entire spectrum, it is possible to only sample for specific Stokes bands to check whether certain expected molecules are present or not. This allows greatly reducing the sampling time.

Further, by adjusting the center frequency and the sweeping range of the first light source 12, one can "zoom into" interesting portions of the spectra as desired. This is particularly true when an FDML laser is used as the first light source, where both, the center frequency as well as the frequency span can be adjusted within certain ranges.

Since the second light source 14 allows generating pump pulses of three different frequencies at 1064 nm, 1122 nm and 1185 nm, this, in combination with an FDML laser having a center frequency at 1310 nm and a frequency span of 150 nm should allow a coverage of Stokes bands from 350 $cm^{-1}$ to 2150 $cm^{-1}$.

Figure 14:
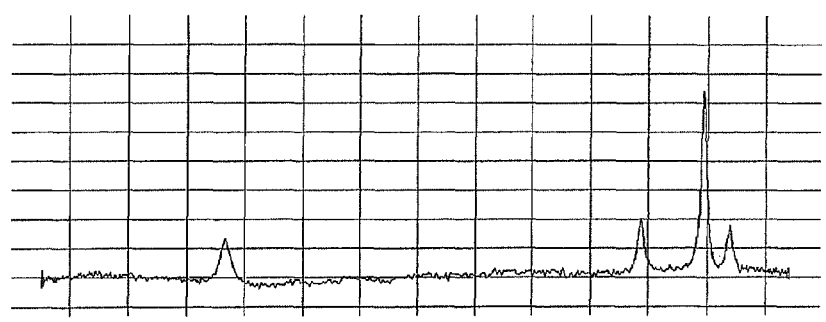
FIG. 14 is a Raman spectrum generated with the system according to one embodiment of the present invention for Toluene.

An enhancement of the spectral coverage from 350 $cm^{-1}$ to 3250 $cm^{-1}$ can be obtained by integrating another FDML laser in the system as is indicated by FIG. 14. In this embodiment, one FDML laser with a center frequency at 1310 nm and one with a center frequency at 1550 nm, each with a 150 nm span are used. Then, in combination with pump pulses of 1064 nm, 1122 nm and 1185 nm, Stokes bands from 350 $cm^{-1}$ to 3250 $cm^{-1}$ can be covered.

Further, since in the system 10 of FIG. 2 both the pump and the probe signals are already delivered in fiber, a big hurdle towards endoscopic applications has been taken. Further, since both light sources are single-mode and in the near IR a good space resolution can be achieved, making this setup ideally usable for Raman microscopy applications.

In FIG. 14, a stimulated Raman spectrum of Toluene is shown which has been recorded with the system of FIG. 2. Shown herein is a partial spectrum which has been obtained with a 1122 nm pump light and a 1310 nm FDML laser probe light with a 57 nm sweep band width. The characteristic Stokes bands of Toluene have been observed.

Figure 15A:
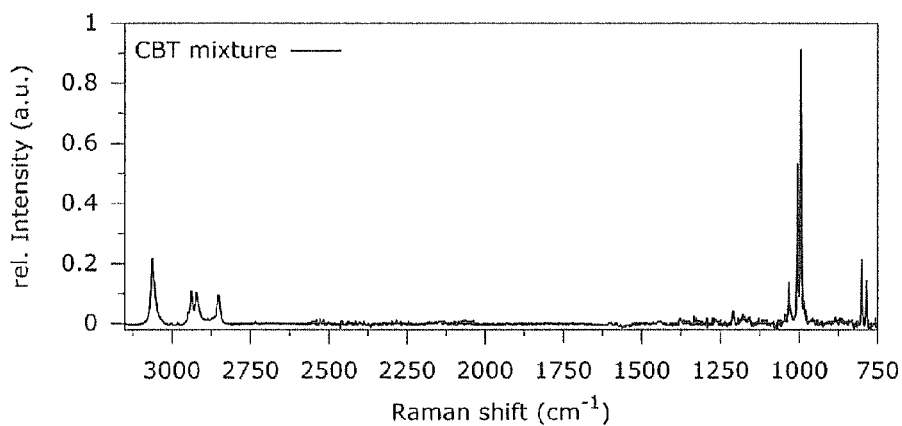
FIG. 15A shows a stimulated Raman emission spectrum of a mixture of equal parts of Cyclohexane, Benzene and Toluene.

FIG. 15A shows a stimulated Raman emission spectrum of a mixture of equal parts of Cyclohexane, Benzene and Toluene, recorded with the system of FIG. 2. As is seen from FIG. 15A, the system of FIG. 2 allows for covering a very large range of Raman shifts from 750 $cm^{-1}$ up to 3150 $cm^{-1}$. This can be obtained using two of the wavelengths provided by the second light source 14 as shown in FIG. 6 (i.e. 1064 nm and 1122 nm) in combination with two sweep ranges of the FDML laser 128 forming the first light source 12 in the system of FIG. 2, where one of the FDML laser sweep ranges was centered at 1300 nm and the other was centered at 1550 nm.

Figure 15B:
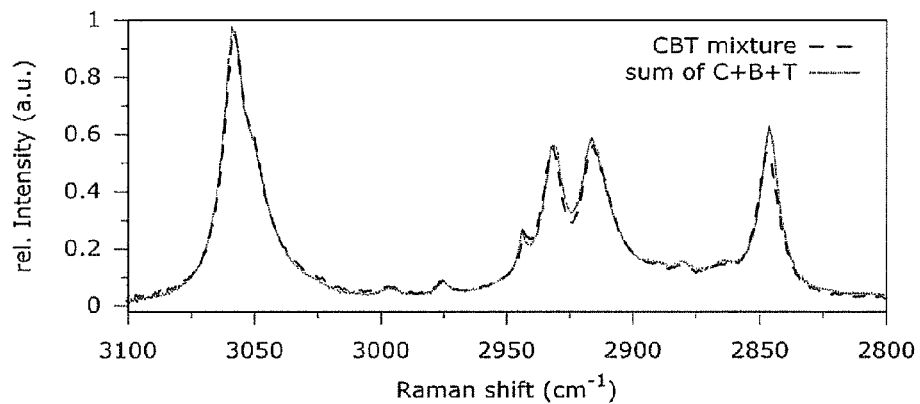
FIG. 15B shows stimulated Raman emission spectra for the individual substances Cyclohexane, Benzene and Toluene.

FIG. 15B shows the stimulated Raman spectra in a range from 2800 to 3100 $cm^{-1}$ for the individual substances Cyclohexane, Benzene and Toluene.

Figure 15C:
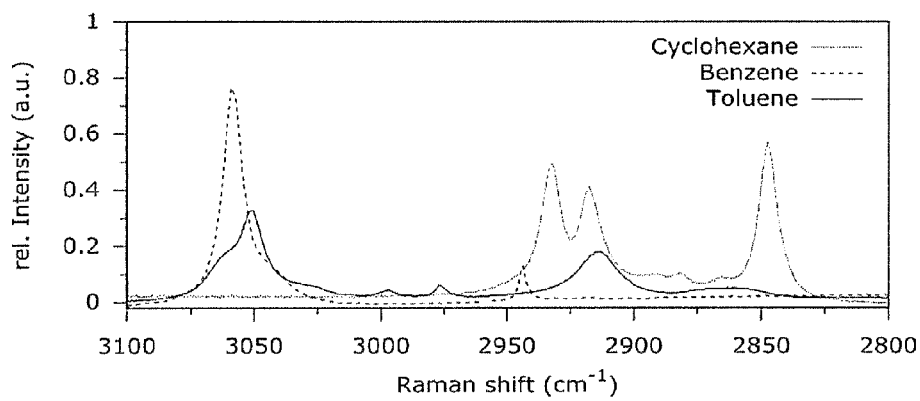
FIG. 15C shows a Raman emission spectrum of the mixture of equal parts of Cyclohexane, Benzene and Toluene as well as the sum of the three individual spectra multiplied by ⅓ of FIG. 15B.

FIG. 15C shows, for the same Raman shift range, the spectrum of the mixture of equal parts of Cyclohexane, Benzene and Toluene with a coarse-hatched line. In addition, FIG. 15C shows with a fine-hatched line the sum of the three individual spectra of FIG. 15B. As is seen in FIG. 15C, the individual spectra when added up almost perfectly match the spectrum of the mixture. In fact, it is seen that the intensity of the stimulated Raman spectrum scales to a very good approximation linearly with the concentration of the respective substance. This demonstrates that the system of FIG. 2 even allows for quantitative analysis of chemical substances by stimulated Raman spectroscopy.

Figure 16A:
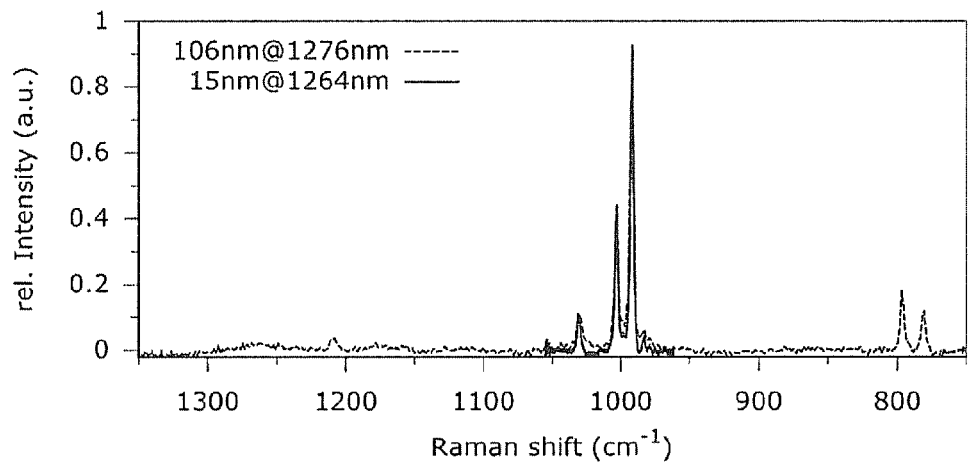
FIG. 16A shows two stimulated Raman spectra of a mixture of Cyclohexane, Benzene and Toluene recorded at two different spectral ranges.
Figure 16B:
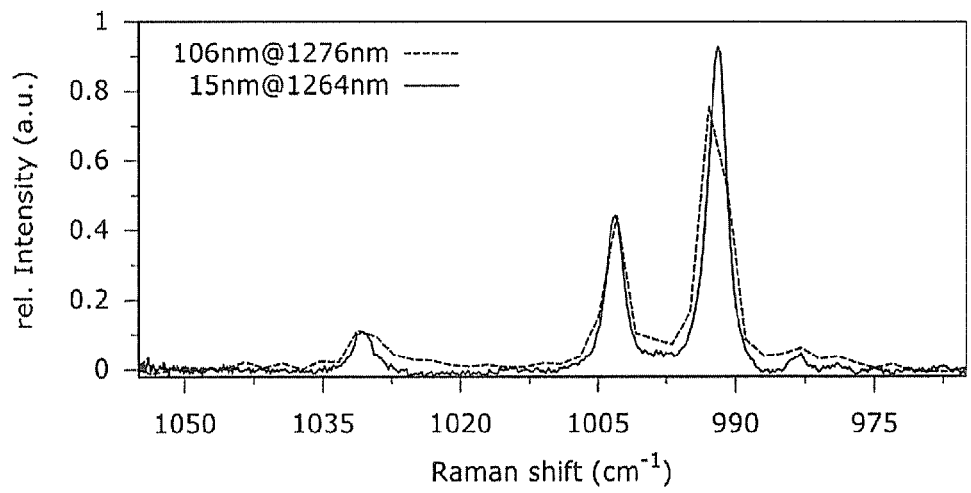
FIG. 16B shows a zoom-in in the same data as FIG. 16A.

In FIG. 16A, again two Raman spectra of the mixture of Cyclohexane, Benzene and Toluene are shown. The spectrum shown with the dashed line has been recorded with a first light source 12 that was formed by an FDML laser having a sweep range of 106 nm centered at 1276 nm. The solid line shows the stimulated Raman spectrum for the same mixture and with the same number of data points, but with a reduced sweep range of 15 nm, centered at 1264 nm, such that the spectral sampling density is increased. FIG. 16B shows the same data as FIG. 16A, but zoomed-in i to show the higher resolved spectrum of FIG. 16A. It is seen how the signal quality improves by increasing the sampling density Importantly, the system of FIG. 2 allows both, scanning large spectral ranges in short times using a lower spectral sampling density as well as zooming into certain spectral ranges of interest with increased spectral sampling density, as becomes particularly apparent from FIG. 16B.

Figure 17:
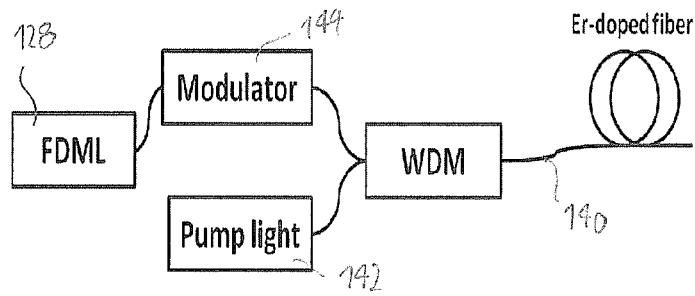
FIG. 17 shows a modification of the first light source comprised of an FDML laser amplified with a doped fiber.

FIG. 17 shows a modification of the first light source 12 comprised of an FDML laser 128 that is amplified using a doped fiber, such as an Erbium-doped fiber 140. The Erbium-doped fiber 140 is pumped using a pump light source 142. The swept light output of the FDML laser 128 is fed into a modulator 144 which can be operated to only transmit the light of the FDML laser 128 in certain time intervals that are synchronized with the pulse signal of the second light source 14 and with the wavelength sweep of the FDML laser 128. This way, a time synchronized, transient amplification can be achieved, allowing for an increase of the stimulated Raman signal.

Instead of using an amplified swept light source as the first light source 12, such as the amplified FDML laser 128 of FIG. 17, it is also possible to use a further light source of the type described for the second light source 14 according to any of the embodiments described herein as the first light source as well. In other words, two of the light sources 14 described above in various embodiments could be employed, one serving as a pump source and one serving as a probe source. This way, high intensity pump and probe signals can be employed. In the embodiments described above, the second light source 14, which in the above embodiments served as the probe light source, was described to be rapidly tunable, as is the case for an FDML laser such as FDML laser 128. However, a light source of the type of the second light source according to one of the embodiments described above can also be made rapidly tunable, e.g. by replacing the seed pulse generation light source (i.e. "first sub-light source"), such as the light source 58 of FIG. 6, by a rapidly tunable light source, such as an FDML laser.

In other applications, the seed light source could be replaced by another tunable, although not necessarily rapidly tunable light source, such as a grating laser. Starting from the seed light source and employing non-linear processes, the light source of the type described above for the second light source 14 allows for obtaining further likewise tunable wavelengths with comparatively high intensities, thereby allowing for increased intensities of the stimulated Raman signals when used as a probe light source, i.e. as the first light source in the previous embodiments. Note that if the seed light source 58 of FIG. 6 is replaced by a rapidly tunable, in particular swept light source, the EOM 64 can be used to select the proper frequency of the swept frequency range.

Figure 18:
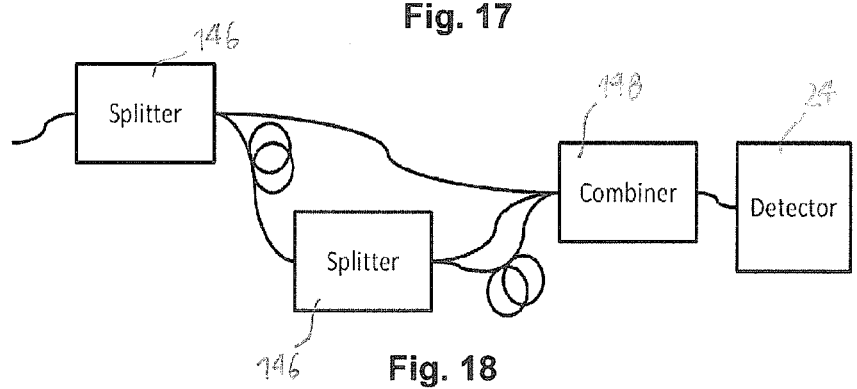
FIG. 18 shows a mechanism for splitting a probe light pulse and transmitting the split pulses with mutual delays to a detector.

FIG. 18 shows an arrangement for splitting the probe light pulse after it has interacted with a sample. The arrangement of FIG. 18 could e.g. replace the fiber 26 and the detector 24 as shown in FIG. 2. The arrangement of FIG. 18 comprises two splitters 146 and a combiner 148. The probe light entering the left splitter 146 in FIG. 18 is split into two signals which are transmitted over different path lengths and thereby mutually delayed with respect to each other. One of the split signals is then split again by the splitter 146 to the right in FIG. 18, and the two split signals are again subjected to different optical path lengths and hence time delayed with respect to each other. This process could be cascaded further (not shown in FIG. 18). All the split signals are then combined at the combiner 148 or at further combiners before they reach the detector 24. In effect, with the mechanism of FIG. 18, the probe signal is split in three or more copies which arrive at the detector 24 at slightly shifted points in time. This way, high intensity probe pulses can be detected at the detector 24 "in pieces" such as to avoid saturation of the detector 24. Clearly, by introducing additional splitters 146 and corresponding delay lines, the probe pulse can be split into any desired number of pulses, thereby limiting the intensity of the individual pulses arriving at the detector 24 and avoiding detector saturation.

Figure 19:
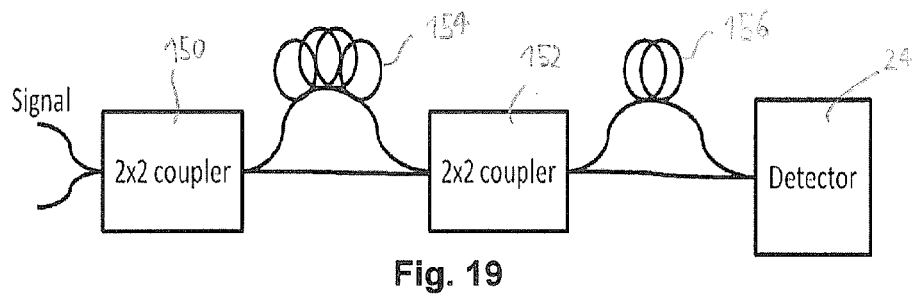
FIG. 19 shows a further mechanism for splitting a probe light pulse and transmitting the split pulses with mutual delays to a detector.

FIG. 19 shows another arrangement for splitting the probe light pulse after it has interacted with the sample. The arrangement consists of two or more 2×2 beam splitters or couplers 150, 152 and multiple delay lines 154, 156. The signal, i.e. the probe pulse, enters a first beam splitter 150 where it is split in two parts. One part is entering a first delay line 154 and the other part is not. Both signals can enter another 2×2 beam splitter 152 where for each part, the light is portioned again and one part is propagating to a second delay line 156 and the other is not. This results in cascaded delay of the signal light where one part of it has no delay, one part has the delay of the first delay line 154, one part has the delay of the second delay line 156, and one part has the delay of both delay lines 154, 156.

Figure 20:
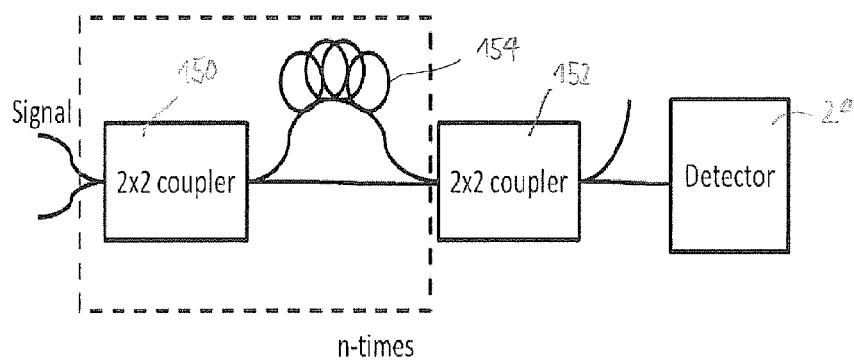
FIG. 20 shows a yet further mechanism for splitting a probe light pulse and transmitting the split pulses with mutual delays to a detector.

A preferred embodiment (shown in FIG. 20) of this delay scheme comprises a first delay line 154 with an optical pathway which is half the inverse repetition rate of the probe pulse. Any further delay stage is constructed in a way to achieve a further delay of half of the previous delay. Accordingly, the delay occasioned by the second delay stage would correspond to ¼ of the inverse repetition rate of the probe pulse. Therefore, n delay stages, each consisting of a 2×2 coupler and a delay path (scaled accordingly to the number n for proper timing) can split the probe pulse in $2^n$ portions. The signal light exiting the last delay stage can then be detected on one or more photodetectors (e.g. using both exits of the 2×2 coupler to detect in parallel). Couplers with even higher splitting numbers can be used, i.e. 3×3 couplers, 4×4 couplers and so on. A second delay arrangement (not shown) can be constructed the same way to provide an identical optical path for a reference light.

A particular advantage of the system of FIG. 2 is that based on the time control of the first and second light sources 12, 14, arbitrary stimulated Raman spectra can be recorded very rapidly. An important application of the system of FIG. 2 would be flow cytometry for detecting evidence for certain diseases, such as cancer, inflammations or HIV from blood samples or the like. For example, cancer cells may contain certain proteins which exhibit a characteristic Raman spectrum that can be used as a "fingerprint" for identifying the cancer cell. With the system of FIG. 2, it becomes possible to specifically sample for certain peaks in the expected Raman spectrum (i.e. "fingerprint") of the cell to be identified, by appropriate synchronization of the first and second light sources 12, 14. For example, several tens or even over a hundred pulses of the second light source 14 could be applied during a single sweep of the first light source 12 at the timings corresponding to the wavelengths of the expected Raman peaks. This can be advantageously combined with further imaging modalities. In particular, the recording of the Raman spectral information can be automatically triggered for individual cells if a possible target cell flowing by is detected by some other imaging modality.

Further modifications to the embodiments described above are possible. For example, the photodiodes 92 of FIGS. 9 and 10 could be replaced by photodiodes having anti-reflective coating, with or without fiber coupling. This way, interferences can be largely suppressed.

In the embodiment of FIG. 10, the probe signal generated by the first light source 12 was split into a measurement beam 99$a$ and a reference beam 99$b$ by means of a 50:50 coupler 100. The measurement and reference beams 99$a$, 99$b$ propagated through the sample 104 with a short time delay such that only the measurement beam 99$a$ would overlap in time with the pump pulse of the second light source 14, but the reference beam 99$b$ would not.

However, instead of separating the measurement beam 99$a$ and the reference beam 99$b$ in time, they can also be separated in space by providing a certain spatial offset, in particular some angular offset such that only the measurement beam 99$a$ overlaps with the probe light beam of the second light source 14.

In a further embodiment, it is possible to measure the Raman-induced Kerr effect by providing for the suitable polarization of the first and second light sources 12, 14 and introducing a polarization analyzer before the detection unit.

In one embodiment, it is advantageous to arrange the optical longpass filter 20 under the Brewster angle, such as to avoid reflections within the filter and interferences caused thereby. Herein, the longpass filter 20 may be a dichroic mirror or the like.

In a further advantageous embodiment, a telescope may be placed downstream of the lens 28 for adjusting the beam diameter in order to avoid an overlap with reflected light and interferences caused thereby.

In a further preferred embodiment, a control or monitoring mechanism is provided for controlling or monitoring the wavelengths of the first and/or second light sources 12, 14 in order to allow for extended measurements without frequency drifts. Further, in one embodiment, a control or monitor device for monitoring the polarization of the first and/or second light sources 12, 14 may be provided.

In a preferred embodiment, the duration of the pulses of the second light source 14 can be adjusted such as to provide an optimum compromise between stimulated Brioullin-scattering and noise of the light source. In order to minimize the noise in the detection, filters, such as a lowpass filter and/or a highpass filter and/or a bandpass filter can be employed. For this, longer pulse lengths of the second light source 14 would be preferable. On the other hand, in order to avoid stimulated Brioullin-scattering, the pulse lengths should be as short as possible. In the system of FIG. 2, very good results were obtained at pulse lengths of 1.8 ns and with the use of a 400 MHz lowpass filter. For these settings, the detected signal was only limited by shot noise.

The embodiments described above and the accompanying figures merely serve to illustrate the system of the present invention, and should not be taken to indicate any limitation thereof. The scope of the patent is solely determined by the following claims.

LIST OF REFERENCE SIGNS

| | |
|---|---|
| 10 | system for stimulated Raman spectroscopy |
| 12 | first light source |
| 14 | second light source |
| 16 | optical assembly |
| 18 | sample location |
| 20 | optical longpass filter |
| 22 | beam dump |
| 24 | detection means |
| 26 | single mode optical fiber |
| 28 | lens |
| 30 | short pass filter |
| 32 | semiconductor optical amplifier |
| 34 | fiber coupler |
| 36 | fiber delay loop |
| 38 | fiber Fabry-Pérot tunable filter |
| 40 | optical isolator |
| 42 | polarization controller |
| 44 | sub-light source |
| 44a | first sub-light source |
| 44b | second sub-light source |
| 44c | third sub-light source |
| 44d | fourth sub-light source |
| 46 | control unit |
| 48 | interaction medium |
| 49 | light output |
| 50 | first amplification stage |
| 52 | wavelength division multiplexer |
| 54 | second amplifier |
| 56 | optical fiber |
| 58 | laser diode |
| 60 | fiber Bragg grating |
| 62 | polarization maintaining fiber |
| 64 | electro-optical modulator |
| 66 | Ytterbium-doped fiber |
| 68 | laser diode |
| 70 | wave division multiplexer |
| 72 | optical isolator |
| 74 | laser line filter |
| 76 | Raman shifting source |
| 78 | laser diode |
| 80 | polarization controller |
| 82 | final amplification stage |
| 84 | double cladding fiber |
| 86 | multi-mode pump source |
| 88 | double-clad-beam combiner |
| 90 | fiber |

LIST OF REFERENCE SIGNS -continued

| | |
|---|---|
| 92 | photo diode |
| 94 | amplifier |
| 95a | probe signal without Raman gain |
| 95b | probe signal with Raman gain |
| 98 | Raman gain signal |
| 99a | measurement beam |
| 99b | reference beam |
| 100 | 50:50 coupler |
| 102 | optical isolator |
| 104 | sample |
| 106 | circulator |
| 108 | free space delay line |
| 110 | double-clad fiber |
| 112 | fiber core |
| 114 | first cladding layer |
| 116 | second cladding layer |
| 118 | lens |
| 120 | moving mirror |
| 122 | rotational axis |
| 124 | sample |
| 126 | function generator |
| 128 | FDML laser |
| 130 | laser diode driver of 1064 nm laser diode |
| 132 | laser diode driver of 1122 nm laser diode |
| 134 | data acquisition card |
| 136 | phase locked loop |
| 138 | pulse generator |
| 140 | Erbium-doped fiber |
| 142 | pump light source |
| 144 | modulator |
| 146 | splitter |
| 148 | combiner |
| 150 | first coupler |
| 152 | second coupler |
| 154 | first delay line |
| 156 | second delay line |

The invention claimed is:

1. A system for measuring light induced transmission or reflection changes, the system comprising a first light source for generating a first light signal having a first wavelength, a second light source for generating a second light signal having a second wavelength, an optical assembly for superposing said first and second light signals at a sample location, and detector for detecting a transmitted or reflected light signal, wherein at least one of the first and second light sources is one or both of actively controllable to emit a time controlled light pattern or operated substantially in CW mode and provided with an extra cavity modulator for generating a time controlled light pattern, and wherein said detector is capable of recording said transmitted or reflected light signal as a function of time.

2. The system of claim 1, wherein at least one of said first and second light sources is adapted for generating a time-varying first or second wavelength, respectively, such as to cause a time-dependent difference between first and second wavelength.

3. The system of claim 2, wherein said system comprises means for reconstructing spectral information from the time information of time-dependent stimulated Raman signal.

4. The system of claim 1, wherein said detector is adapted to record said transmitted or reflected light signal by means of a time-gated detection.

5. The system of claim 4, wherein the second light source is adapted to generate light pulses with a predetermined timing, said second light source being synchronized with said first light source such as to provide for a controlled timing of the second light source pulses with regard to a wavelength sweep or stepwise tuning of the first light source.

6. The system of claim 5, wherein the time gap between consecutive pulses can be independently chosen.

7. The system of claim 5, wherein the timing of the pulses of the second light source with respect to the wavelength sweeps of the first light source is electronically configurable.

8. The system of claim 5, wherein the synchronization of
the first and second light sources and/or
the second light source and the detector is established electronically.

9. The system of claim 8, wherein the system comprises an electronic function generator for generating electronic signals for operation of one or more of the first light source, the second light source, and an analogue-to-digital converter of said detector.

10. The system of claim 5, wherein the second light source is synchronized with one or more of a sample clock, a sample time gate, a multiplicative time trace or an acquisition trigger associated with the detector.

11. The system of claim 4, wherein the first light source is one of an Fourier domain model locking (FDML) laser, a vertical cavity surface emitting laser (VCSEL), a tunable external cavity semiconductor laser or a tunable Vernier diode laser.

12. The system of claim 1, wherein the first light source is a wavelength sweeping light source.

13. The system of claim 12, wherein the first light source is adapted to carry out a periodic wavelength sweep of at least 0.1 kHz.

14. The system of claim 1, wherein the second light source is synchronized with the detector.

15. The system of claim 1, wherein the detector comprises a differential photo detector, wherein the differential photo detector is arranged to detect a difference between
a reference signal generated when none or only one of the first and second light signals passes the sample, and
a measurement signal generated when both light signals pass the sample.

16. The system of claim 1, wherein the second light source comprises:
at least two sub-light sources which are controllable by an electronic control unit,
an interaction medium coupled with said sub-light sources such that due to interaction with the interaction medium and in response to the control of said electronic control unit, at least one of
an output wavelength,
a time dependent intensity or
a polarisation state of said second light source can be controlled, wherein the second light source comprises a first sub-light source and the modulator for modulating light generated by the first sub-light source, wherein said modulator can be electronically controlled to generate a light pulse pattern, wherein the pulse lengths of the light pulse pattern are between 5 ps and 20 ns.

17. The system of claim 1, wherein said light induced transmission or reflection change is due to stimulated Raman emission, wherein the detector is for detecting a stimulated Raman signal caused by a Raman active medium when located at said sample location, and wherein said detector is capable of recording said stimulated Raman signal as a function of time.

18. The system of claim 17, wherein said light induced transmission or reflection change is due to stimulated Raman emission, wherein the detector is for detecting a stimulated Raman signal caused by a Raman active medium is located at said sample location, and wherein said detector is capable of recording said stimulated Raman signal as a function of time.

19. A method for measuring light induced transmission and reflection changes, the method comprising: generating a first light signal having a first wavelength using a first light source, generating a second light signal having a second wavelength using a second light source, superposing said first and second light signals at a sample location, and detecting a transmitted or reflected light signal, wherein at least one of the first and second light sources is one or both of actively controllable to emit a time controlled light pattern or operated substantially in CW mode and provided with an extra cavity modulator for generating a time controlled light pattern, and wherein the transmitted or reflected light signal is recorded as a function of time.

20. The method of claim 19, wherein spectral information is reconstructed from the said transmitted or reflected signal.

* * * * *

UNITED STATES PATENT AND TRADEMARK OFFICE
CERTIFICATE OF CORRECTION

PATENT NO. : 9,638,638 B2
APPLICATION NO. : 14/890109
DATED : May 2, 2017
INVENTOR(S) : Robert Alexander Huber et al.

Page 1 of 1

It is certified that error appears in the above-identified patent and that said Letters Patent is hereby corrected as shown below:

In the Claims

At Column 29, Line 21, "an Fourier domain model" should be -- a Fourier domain mode --.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*